United States Patent
Goble et al.

(12) 
(10) Patent No.: US 6,565,561 B1
(45) Date of Patent: May 20, 2003

(54) ELECTROSURGICAL INSTRUMENT

(75) Inventors: Nigel M. Goble, Wales (GB); Colin C. O. Goble, Wales (GB); Alan N. Syrop, Wales (GB)

(73) Assignee: Cyrus Medical Limited, Cardiff (GB)

( * ) Notice: Subject to any disclaimer, the term of this patent is extended or adjusted under 35 U.S.C. 154(b) by 0 days.

(21) Appl. No.: 09/541,514

(22) Filed: Apr. 3, 2000

Related U.S. Application Data

(63) Continuation-in-part of application No. 09/115,675, filed on Jul. 15, 1998, now abandoned, which is a continuation-in-part of application No. 09/462,926, filed as application No. PCT/GB98/02081 on Jan. 18, 2000, which is a continuation-in-part of application No. 09/202,025, filed as application No. PCT/GB97/01632 on Dec. 8, 1998, now Pat. No. 6,210,405.

(30) Foreign Application Priority Data

| Jun. 20, 1996 | (GB) | 9612993 |
| Jul. 18, 1997 | (GB) | 9715197 |
| Jul. 18, 1997 | (GB) | 97115199 |
| Dec. 19, 1997 | (GB) | 9726952 |
| Jul. 7, 1998 | (GB) | 9814727 |

(51) Int. Cl.[7] .............................................. A61B 18/18
(52) U.S. Cl. ............................ 606/41; 606/45; 606/46; 606/47; 606/48; 606/49; 607/101; 607/104; 607/105
(58) Field of Search .............................. 606/1, 41, 42, 606/45–50, 170, 171, 180; 607/101, 104, 105; 604/22

(56) References Cited

U.S. PATENT DOCUMENTS

| 164,184 | A | 6/1875 | Kidder |
| 1,366,756 | A | 1/1921 | Wappler |
| 1,735,271 | A | 11/1929 | Groff |
| 1,814,791 | A | 7/1931 | Ende |
| 1,889,609 | A | 11/1932 | Mutscheller |
| 1,932,258 | A | 10/1933 | Wappler |
| 1,943,543 | A | 1/1934 | McFadden |
| 1,952,617 | A | 3/1934 | Wappler |
| 1,983,669 | A | 12/1934 | Kimble |
| 2,050,904 | A | 8/1936 | Trice |
| 2,056,377 | A | 10/1936 | Wappler |
| 2,196,171 | A | 4/1940 | Arnesen |
| 2,888,928 | A | 6/1959 | Seiger |
| 3,035,580 | A | 5/1962 | Guiorguiev |
| 3,460,539 | A | 8/1969 | Anhalt, Sr. |
| 3,595,239 | A | 7/1971 | Petersen |
| 3,601,126 | A | 8/1971 | Estes |

(List continued on next page.)

FOREIGN PATENT DOCUMENTS

| CH | 243478 | 7/1946 |
| DE | 651428 | 9/1937 |
| DE | 949370 | 3/1956 |

(List continued on next page.)

OTHER PUBLICATIONS

Cook, Albert M. & John G. Webster, *Therapeutic Medical Devices Application and Design*, Prentice–Hall Inc., New Jersey, 1982, p. 349.

(List continued on next page.)

*Primary Examiner*—Rosiland S. Kearney
(74) *Attorney, Agent, or Firm*—Nixon & Vanderhye P.C.

(57) ABSTRACT

An electrosurgical instrument is provided for the treatment of tissue in the presence of an electrically-conductive fluid medium. The instrument comprises an instrument shaft (10), and a tissue treatment electrode (12) at the distal end of the shaft for electrosurgically excising tissue pieces at an operation site. The tissue treatment electrode (12) is cyclically movable relative to the distal end of the shaft (10). Threshold control means are provided for controlling the power threshold for vaporisation of the electrically-conductive fluid medium at the tissue treatment electrode (12).

24 Claims, 8 Drawing Sheets

U.S. PATENT DOCUMENTS

| | | |
|---|---|---|
| 3,614,414 A | 10/1971 | Gores |
| 3,648,001 A | 3/1972 | Anderson et al. |
| 3,685,518 A | 8/1972 | Beurle et al. |
| 3,699,967 A | 10/1972 | Anderson |
| 3,707,149 A | 12/1972 | Hao et al. |
| 3,801,766 A | 4/1974 | Morrison, Jr. |
| 3,815,604 A | 6/1974 | O'Malley et al. |
| 3,845,771 A | 11/1974 | Vise |
| 3,847,153 A | 11/1974 | Weissman |
| 3,870,047 A | 3/1975 | Gonser |
| 3,885,569 A | 5/1975 | Judson |
| 3,898,991 A | 8/1975 | Ikuno et al. |
| 3,901,242 A | 8/1975 | Storz |
| 3,902,494 A | 9/1975 | Haberlen et al. |
| 3,903,891 A | 9/1975 | Brayshaw |
| 3,920,021 A | 11/1975 | Hiltebrandt |
| 3,920,022 A | 11/1975 | Pastor |
| 3,923,063 A | 12/1975 | Andrews et al. |
| 3,929,137 A | 12/1975 | Gonser et al. |
| 3,939,839 A | 2/1976 | Curtiss |
| 3,945,375 A | 3/1976 | Banko |
| 3,963,030 A | 6/1976 | Newton |
| 3,964,487 A | 6/1976 | Judson |
| 3,970,088 A | 7/1976 | Morrison |
| 3,974,833 A | 8/1976 | Durden, III |
| 4,011,872 A | 3/1977 | Komiya |
| 4,016,881 A | 4/1977 | Rioux et al. |
| 4,024,467 A | 5/1977 | Andrews et al. |
| 4,033,351 A | 7/1977 | Hetzel |
| 4,040,426 A | 8/1977 | Morrison, Jr. |
| 4,043,342 A | 8/1977 | Morrison, Jr. |
| 4,051,855 A | 10/1977 | Schneiderman |
| 4,060,088 A | 11/1977 | Morrison, Jr. et al. |
| 4,069,827 A | 1/1978 | Dominy |
| 4,074,718 A | 2/1978 | Morrison, Jr. |
| 4,092,986 A | 6/1978 | Schneiderman |
| 4,114,623 A | 9/1978 | Meinke et al. |
| 4,116,198 A | 9/1978 | Roos |
| 4,119,102 A | 10/1978 | LeVeen |
| 4,126,137 A | 11/1978 | Archibald |
| 4,154,240 A | 5/1979 | Ikuno et al. |
| 4,189,685 A | 2/1980 | Doss |
| 4,200,104 A | 4/1980 | Harris |
| 4,202,337 A | 5/1980 | Hren et al. |
| 4,204,549 A | 5/1980 | Paglione |
| 4,210,152 A | 7/1980 | Berry |
| 4,228,800 A | 10/1980 | Degler, Jr. et al. |
| 4,248,231 A | 2/1981 | Herczog et al. |
| 4,271,837 A | 6/1981 | Schuler |
| 4,281,373 A | 7/1981 | Mabille |
| 4,301,802 A | 11/1981 | Poler |
| 4,326,529 A | 4/1982 | Doss et al. |
| 4,346,332 A | 8/1982 | Walden |
| 4,376,263 A | 3/1983 | Pittroff et al. |
| 4,381,007 A | 4/1983 | Doss |
| 4,416,277 A | 11/1983 | Newton et al. |
| 4,418,692 A | 12/1983 | Guay |
| 4,429,698 A | 2/1984 | Bentall |
| 4,448,198 A | 5/1984 | Turner |
| 4,474,179 A | 10/1984 | Koch |
| 4,476,862 A | 10/1984 | Pao |
| 4,492,231 A | 1/1985 | Auth |
| 4,494,541 A | 1/1985 | Archibald |
| 4,512,338 A | 4/1985 | Balko et al. |
| 4,517,976 A | 5/1985 | Murakoshi et al. |
| 4,524,770 A | 6/1985 | Orandi |
| 4,532,924 A | 8/1985 | Auth et al. |
| 4,534,347 A | 8/1985 | Taylor |
| 4,548,207 A | 10/1985 | Reimels |
| 4,559,943 A | 12/1985 | Bowers |
| 4,559,951 A | 12/1985 | Dahl et al. |
| 4,562,838 A | 1/1986 | Walker |
| 4,565,200 A | 1/1986 | Cosman |
| 4,567,890 A | 2/1986 | Ohta et al. |
| 4,580,557 A | 4/1986 | Hertzmann |
| 4,590,934 A | 5/1986 | Malis et al. |
| 4,593,691 A | 6/1986 | Lindstrom et al. |
| 4,617,927 A | 10/1986 | Manes |
| 4,657,015 A | 4/1987 | Irnich |
| 4,658,819 A | 4/1987 | Harris et al. |
| 4,658,820 A | 4/1987 | Klicek |
| 4,669,468 A | 6/1987 | Cartmell et al. |
| 4,674,499 A | 6/1987 | Pao |
| 4,681,122 A | 7/1987 | Winters et al. |
| 4,682,596 A | 7/1987 | Bales et al. |
| 4,688,569 A | 8/1987 | Rabinowitz |
| 4,696,668 A | 9/1987 | Wilcox |
| 4,706,667 A | 11/1987 | Roos |
| 4,709,698 A | 12/1987 | Johnston et al. |
| 4,712,544 A | 12/1987 | Ensslin |
| 4,727,874 A | 3/1988 | Bowers et al. |
| 4,735,201 A | 4/1988 | O'Reilly |
| 4,739,759 A | 4/1988 | Rexroth et al. |
| 4,769,005 A | 9/1988 | Ginsburg et al. |
| 4,781,175 A | 11/1988 | McGreevy et al. |
| 4,799,480 A | 1/1989 | Abraham et al. |
| 4,800,899 A | 1/1989 | Elliott |
| 4,802,476 A | 2/1989 | Noerenberg et al. |
| 4,805,616 A | 2/1989 | Pao |
| 4,813,429 A | 3/1989 | Eshel et al. |
| 4,815,462 A | 3/1989 | Clark |
| 4,820,298 A | 4/1989 | Leveen et al. |
| 4,823,791 A | 4/1989 | D'Amelio et al. |
| 4,827,927 A | 5/1989 | Newton |
| 4,832,048 A | 5/1989 | Cohen |
| 4,850,353 A | 7/1989 | Stasz et al. |
| 4,860,744 A | 8/1989 | Johnson et al. |
| 4,878,493 A | 11/1989 | Pasternak et al. |
| 4,886,074 A | 12/1989 | Bisping |
| 4,919,129 A | 4/1990 | Weber, Jr. et al. |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,936,310 A | 6/1990 | Engstrom et al. |
| 4,936,842 A | 6/1990 | D'Amelio et al. |
| 4,943,290 A | 7/1990 | Rexroth et al. |
| 4,950,267 A | 8/1990 | Ishihara et al. |
| 4,955,377 A | 9/1990 | Lennox et al. |
| 4,966,597 A | 10/1990 | Cosman |
| 4,967,765 A | 11/1990 | Turner et al. |
| 4,969,885 A | 11/1990 | Farin |
| 4,976,711 A | 12/1990 | Parins et al. |
| 4,994,069 A | 2/1991 | Ritchart et al. |
| 4,998,933 A | 3/1991 | Eggers et al. |
| 5,007,908 A | 4/1991 | Rydell |
| 5,009,656 A | 4/1991 | Reimels |
| 5,013,312 A | 5/1991 | Parins et al. |
| 5,019,076 A | 5/1991 | Yamanashi et al. |
| 5,035,696 A | 7/1991 | Rydell |
| 5,037,379 A | 8/1991 | Clayman et al. |
| 5,047,026 A | 9/1991 | Rydell |
| 5,047,027 A | 9/1991 | Rydell |
| 5,057,107 A | 10/1991 | Parins et al. |
| 5,062,031 A | 10/1991 | Flachenecker et al. |
| 5,071,418 A | 12/1991 | Rosenbaum |
| 5,080,660 A | 1/1992 | Buelna |
| 5,083,565 A | 1/1992 | Parins |
| 5,085,659 A | 2/1992 | Rydell |
| 5,088,997 A | 2/1992 | Delahuerga et al. |
| 5,098,431 A | 3/1992 | Rydell |

| Patent No. | Date | Inventor |
|---|---|---|
| 5,099,840 A | 3/1992 | Goble et al. |
| 5,108,391 A | 4/1992 | Flachenecker et al. |
| 5,108,407 A | 4/1992 | Geremia et al. |
| RE33,925 E | 5/1992 | Bales et al. |
| 5,117,978 A | 6/1992 | Blumenfeld et al. |
| 5,122,138 A | 6/1992 | Manwaring |
| 5,133,365 A | 7/1992 | Heil, Jr. et al. |
| 5,133,713 A | 7/1992 | Huang et al. |
| 5,158,561 A | 10/1992 | Rydell et al. |
| 5,167,658 A | 12/1992 | Ensslin |
| 5,167,659 A | 12/1992 | Ohtomo et al. |
| 5,171,255 A | 12/1992 | Rydell |
| 5,171,311 A | 12/1992 | Rydell et al. |
| 5,178,620 A | 1/1993 | Eggers et al. |
| 5,190,517 A | 3/1993 | Zieve et al. |
| 5,195,959 A | 3/1993 | Smith |
| 5,196,007 A | 3/1993 | Ellman et al. |
| 5,197,963 A | 3/1993 | Parins |
| 5,201,743 A | 4/1993 | Haber et al. |
| 5,207,675 A | 5/1993 | Canady |
| 5,211,625 A | 5/1993 | Sakurai et al. |
| 5,217,457 A | 6/1993 | Delahuerga et al. |
| 5,217,458 A | 6/1993 | Parins |
| 5,217,459 A | 6/1993 | Kamerling |
| 5,221,281 A | 6/1993 | Klicek |
| 5,244,462 A | 9/1993 | Delahuerga et al. |
| 5,249,585 A | 10/1993 | Turner et al. |
| 5,250,047 A | 10/1993 | Rydell |
| 5,257,990 A | 11/1993 | Nash |
| 5,258,006 A | 11/1993 | Rydell et al. |
| 5,259,395 A | 11/1993 | Li |
| 5,261,906 A | 11/1993 | Pennino et al. |
| 5,267,994 A | 12/1993 | Gentelia et al. |
| 5,267,997 A | 12/1993 | Farin et al. |
| 5,277,201 A | 1/1994 | Stern |
| 5,277,696 A | 1/1994 | Hagen |
| 5,281,213 A | 1/1994 | Milder et al. |
| 5,281,216 A | 1/1994 | Klicek |
| 5,282,799 A | 2/1994 | Rydell |
| 5,282,845 A | 2/1994 | Bush et al. |
| 5,290,282 A | 3/1994 | Casscells |
| 5,290,283 A | 3/1994 | Suda |
| 5,300,068 A | 4/1994 | Rosar et al. |
| 5,300,069 A | 4/1994 | Hunsberger et al. |
| 5,300,070 A | 4/1994 | Gentelia et al. |
| 5,304,214 A | 4/1994 | DeFord et al. |
| 5,306,238 A | 4/1994 | Fleenor |
| 5,317,155 A | 5/1994 | King |
| 5,318,563 A | 6/1994 | Malis et al. |
| 5,320,627 A | 6/1994 | Sorensen et al. |
| 5,330,470 A | 7/1994 | Hagen |
| 5,330,471 A | 7/1994 | Eggers |
| 5,334,193 A | 8/1994 | Nardella |
| 5,334,198 A | 8/1994 | Hart et al. |
| 5,336,222 A | 8/1994 | Durgin, Jr. et al. |
| 5,342,357 A | 8/1994 | Nardella |
| 5,342,391 A | 8/1994 | Foshee et al. |
| 5,344,428 A | 9/1994 | Griffiths |
| 5,352,222 A | 10/1994 | Rydell |
| 5,354,296 A | 10/1994 | Turkel |
| 5,364,395 A | 11/1994 | West, Jr. |
| 5,366,443 A | 11/1994 | Eggers et al. |
| 5,370,645 A | 12/1994 | Klicek et al. |
| 5,370,675 A | 12/1994 | Edwards et al. |
| 5,372,596 A | 12/1994 | Klicek et al. |
| 5,382,247 A | 1/1995 | Cimino et al. |
| 5,383,874 A | 1/1995 | Jackson et al. |
| 5,383,876 A | 1/1995 | Nardella |
| 5,383,917 A | 1/1995 | Desai et al. |
| 5,383,923 A | 1/1995 | Webster, Jr. |
| 5,395,363 A | 3/1995 | Billings et al. |
| 5,395,368 A | 3/1995 | Ellman et al. |
| 5,403,311 A | 4/1995 | Abele et al. |
| 5,419,767 A | 5/1995 | Eggers et al. |
| 5,422,567 A | 6/1995 | Matsunaga |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,431,649 A | 7/1995 | Mulier et al. |
| 5,437,662 A | 8/1995 | Nardella |
| 5,438,302 A | 8/1995 | Goble |
| 5,441,499 A | 8/1995 | Fritzsch |
| 5,441,503 A | 8/1995 | Considine et al. |
| 5,443,470 A | 8/1995 | Stern et al. |
| 5,451,223 A | 9/1995 | Ben-Simhon |
| 5,454,809 A | 10/1995 | Janssen |
| 5,462,521 A | 10/1995 | Brucker et al. |
| 5,472,441 A | 12/1995 | Edwards et al. |
| 5,472,443 A | 12/1995 | Cordis et al. |
| 5,480,397 A | 1/1996 | Eggers et al. |
| 5,480,398 A | 1/1996 | Eggers et al. |
| 5,496,312 A | 3/1996 | Klicek |
| 5,496,314 A | 3/1996 | Eggers |
| 5,505,728 A | 4/1996 | Ellman et al. |
| 5,505,730 A | 4/1996 | Edwards |
| 5,507,743 A | 4/1996 | Edwards et al. |
| 5,514,129 A | 5/1996 | Smith |
| 5,514,130 A | 5/1996 | Baker |
| 5,514,131 A | 5/1996 | Edwards et al. |
| 5,520,684 A | 5/1996 | Imran |
| 5,520,685 A | 5/1996 | Wojciechowicz |
| 5,522,815 A | 6/1996 | Durgin, Jr. et al. |
| 5,527,331 A | 6/1996 | Kresch et al. |
| 5,531,744 A | 7/1996 | Nardella et al. |
| 5,536,267 A | 7/1996 | Edwards et al. |
| 5,540,680 A | 7/1996 | Guglielmi et al. |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,540,685 A | 7/1996 | Parins et al. |
| 5,542,916 A | 8/1996 | Hirsch et al. |
| 5,542,945 A | 8/1996 | Fritzsch |
| 5,545,161 A | 8/1996 | Imran |
| 5,545,193 A | 8/1996 | Fleischman et al. |
| 5,549,605 A | 8/1996 | Hahnen |
| 5,554,172 A | 9/1996 | Horner et al. |
| 5,555,618 A | 9/1996 | Winkler |
| 5,556,396 A | 9/1996 | Cohen et al. |
| 5,556,397 A | 9/1996 | Long et al. |
| 5,558,671 A | 9/1996 | Yates |
| 5,562,720 A | 10/1996 | Stern et al. |
| 5,569,164 A | 10/1996 | Lurz |
| 5,569,242 A | 10/1996 | Lax et al. |
| 5,569,244 A | 10/1996 | Hahnen |
| 5,569,245 A | 10/1996 | Guglielmi et al. |
| 5,571,100 A | 11/1996 | Goble et al. |
| 5,575,789 A | 11/1996 | Bell et al. |
| 5,578,007 A | 11/1996 | Imran |
| 5,582,609 A | 12/1996 | Swanson et al. |
| 5,582,610 A | 12/1996 | Grossi et al. |
| 5,584,830 A | 12/1996 | Ladd et al. |
| 5,591,141 A | 1/1997 | Nettekoven |
| 5,599,344 A | 2/1997 | Paterson |
| 5,599,345 A | 2/1997 | Edwards et al. |
| 5,599,346 A | 2/1997 | Edwards et al. |
| 5,599,347 A | 2/1997 | Hart et al. |
| 5,599,348 A | 2/1997 | Gentelia et al. |
| 5,599,349 A | 2/1997 | D'Amelio |
| 5,603,711 A | 2/1997 | Parins et al. |
| 5,603,712 A | 2/1997 | Koranda et al. |

| | | | |
|---|---|---|---|
| 5,607,422 A | 3/1997 | Smeets et al. | |
| 5,609,151 A | 3/1997 | Mulier et al. | |
| 5,609,573 A | 3/1997 | Sandock | |
| 5,611,798 A | 3/1997 | Eggers | |
| 5,620,481 A | 4/1997 | Desai et al. | |
| 5,624,439 A | 4/1997 | Edwards et al. | |
| 5,626,560 A | 5/1997 | Soring | |
| 5,626,575 A | 5/1997 | Crenner | |
| 5,626,576 A | 5/1997 | Janssen | |
| 5,626,578 A | 5/1997 | Tihon | |
| 5,628,745 A | 5/1997 | Bek | |
| 5,628,771 A | 5/1997 | Mizukawa et al. | |
| 5,630,426 A | 5/1997 | Eggers et al. | |
| 5,633,578 A | 5/1997 | Eggers et al. | |
| 5,634,924 A | 6/1997 | Turkel et al. | |
| 5,647,869 A | 7/1997 | Goble et al. | |
| 5,672,174 A | 9/1997 | Gough et al. | |
| 5,683,366 A | 11/1997 | Eggers et al. | |
| 5,693,045 A | 12/1997 | Eggers | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,700,262 A | 12/1997 | Acosta et al. | |
| 5,725,524 A | 3/1998 | Mulier et al. | |
| 5,735,846 A | 4/1998 | Panescu et al. | |
| 5,766,153 A | 6/1998 | Eggers et al. | |
| 5,776,092 A | 7/1998 | Farin et al. | |
| 5,792,140 A | 8/1998 | Tu et al. | |
| 5,797,901 A | * 8/1998 | Cosmescu | 604/35 |
| 5,810,764 A | 9/1998 | Eggers et al. | |
| 5,810,809 A | 9/1998 | Rydell | |
| 5,814,044 A | * 9/1998 | Hooven | 604/21 |
| 5,830,214 A | 11/1998 | Flom et al. | |
| 5,833,689 A | 11/1998 | Long | |
| 5,843,019 A | 12/1998 | Eggers et al. | |
| 5,860,951 A | 1/1999 | Eggers et al. | |
| 5,871,469 A | 2/1999 | Eggers et al. | |
| 5,873,855 A | 2/1999 | Eggers et al. | |
| 5,888,198 A | 3/1999 | Eggers et al. | |
| 5,891,095 A | 4/1999 | Eggers et al. | |
| 5,902,272 A | 5/1999 | Eggers et al. | |
| 5,904,681 A | 5/1999 | West, Jr. | |
| 5,910,150 A | * 6/1999 | Saadat | 604/22 |
| 5,919,188 A | 7/1999 | Shearon et al. | |
| 5,941,876 A | 8/1999 | Nardella et al. | |
| 5,941,893 A | 8/1999 | Saadat | |
| 6,093,186 A | 7/2000 | Goble | |

FOREIGN PATENT DOCUMENTS

| | | |
|---|---|---|
| DE | 1007960 | 5/1957 |
| DE | 2222820 | 11/1973 |
| DE | 2457900 | 5/1976 |
| DE | 2930982 | 2/1981 |
| DE | 3209444 | 10/1982 |
| DE | 3215832 A | 11/1982 |
| DE | 3119735 | 1/1983 |
| DE | 3245570 | 6/1984 |
| DE | 222207 | 5/1985 |
| DE | 3423356 | 1/1986 |
| DE | 3427517 | 1/1986 |
| DE | 3511107 | 10/1986 |
| DE | 3623688 | 1/1987 |
| DE | 3530335 | 3/1987 |
| DE | 3707820 | 9/1987 |
| DE | 3622337 C2 | 1/1988 |
| DE | 3642077 C2 | 6/1988 |
| DE | 3708801 C2 | 9/1988 |
| DE | 3824913 | 2/1990 |
| DE | 3838840 C2 | 5/1990 |
| DE | 3930451 | 3/1991 |
| DE | 4108269 C2 | 6/1992 |
| DE | 4103972 C2 | 8/1992 |
| DE | 4126608 | 2/1993 |
| DE | 4139029 C2 | 6/1993 |
| DE | 4217999 A1 | 12/1993 |
| DE | 4237321 A1 | 5/1994 |
| DE | 4323585 | 1/1995 |
| DE | 4339049 | 5/1995 |
| DE | 4425015 | 1/1996 |
| DE | 4429478 | 3/1996 |
| DE | 19530004 A | 3/1996 |
| DE | 19510185 A | 10/1996 |
| DE | 19512640 C2 | 10/1996 |
| DE | 19514552 A | 10/1996 |
| DE | 19514553 C1 | 10/1996 |
| DE | 19526243 C1 | 1/1997 |
| DE | 19526244 | 1/1997 |
| DE | 19543547 C1 | 1/1997 |
| DE | 19630601 | 2/1997 |
| DE | 29617461 U | 2/1997 |
| DE | 19537897 A | 3/1997 |
| DE | 19542417 A | 5/1997 |
| DE | 19542418 A | 5/1997 |
| DE | 19542419 A | 5/1997 |
| DE | 19545539 A | 6/1997 |
| DE | 19545756 A | 6/1997 |
| DE | 19650797 A | 6/1997 |
| EP | 0 013605 | 7/1980 |
| EP | 0 049633 | 4/1982 |
| EP | 0 067680 | 12/1982 |
| EP | 0 136855 | 4/1985 |
| EP | 0 219568 | 12/1985 |
| EP | 0 205851 | 12/1986 |
| EP | 0 280798 A | 9/1988 |
| EP | 0 310431 | 4/1989 |
| EP | 0 316469 | 5/1989 |
| EP | 0 325456 | 7/1989 |
| EP | 0 332308 | 9/1989 |
| EP | 0 373670 | 6/1990 |
| EP | 0 392837 | 10/1990 |
| EP | 0 407057 | 1/1991 |
| EP | 0 412426 | 2/1991 |
| EP | 0 437377 | 7/1991 |
| EP | 0 448798 | 10/1991 |
| EP | 0 448857 | 10/1991 |
| EP | 0 499491 | 8/1992 |
| EP | 0 507622 | 10/1992 |
| EP | 0 509670 | 10/1992 |
| EP | 0 517243 | 12/1992 |
| EP | 0 518230 | 12/1992 |
| EP | 0 530400 | 3/1993 |
| EP | 0 536440 | 4/1993 |
| EP | 0 558316 | 9/1993 |
| EP | 0 558318 | 9/1993 |
| EP | 0 647435 | 4/1995 |
| EP | 0 653192 | 5/1995 |
| EP | 0 674909 | 10/1995 |
| EP | 0 684015 | 11/1995 |
| EP | 0 688536 | 12/1995 |
| EP | 0 692224 | 1/1996 |
| EP | 0 694290 | 1/1996 |
| EP | 0 697199 | 2/1996 |
| EP | 0 709065 | 5/1996 |
| EP | 0 714635 | 6/1996 |
| EP | 0 717967 | 6/1996 |
| EP | 0 732080 | 9/1996 |
| EP | 0 733345 | 9/1996 |
| EP | 0 737447 | 10/1996 |
| EP | 0 740926 | 11/1996 |
| EP | 0 754437 | 1/1997 |
| FR | 57862 | 9/1953 |

| | | |
|---|---|---|
| FR | 1215305 | 4/1960 |
| FR | 1454773 | 10/1966 |
| FR | 2313949 | 1/1977 |
| FR | 2443829 | 7/1980 |
| FR | 2501034 | 9/1982 |
| FR | 2645008 | 10/1990 |
| GB | 1361497 | 7/1974 |
| GB | 2037167 | 7/1980 |
| GB | 1583397 | 1/1981 |
| GB | 2084880 | 4/1982 |
| GB | 2101893 | 1/1983 |
| GB | 2133290 | 7/1984 |
| GB | 2145932 | 4/1985 |
| GB | 2161081 | 1/1986 |
| GB | 2164473 | 3/1986 |
| GB | 2165761 | 4/1986 |
| GB | 2177309 | 1/1987 |
| GB | 2179861 | 3/1987 |
| GB | 2213381 | 8/1989 |
| GB | 2214430 | 9/1989 |
| GB | 2269538 | 2/1994 |
| JP | 62211060 | 9/1987 |
| RU | 644491 | 1/1979 |
| WO | WO 81/03271 | 11/1981 |
| WO | WO 82/00084 | 1/1982 |
| WO | WO 82/02488 | 8/1982 |
| WO | WO 84/03829 | 10/1984 |
| WO | WO 88/01851 | 3/1988 |
| WO | WO 90/03152 | 4/1990 |
| WO | WO 93/08756 | 5/1993 |
| WO | WO 93/13718 | 7/1993 |
| WO | WO 93/13816 | 7/1993 |
| WO | WO 93/16650 | 9/1993 |
| WO | WO 93/19681 | 10/1993 |
| WO | WO 93/19682 | 10/1993 |
| WO | WO 93/20747 | 10/1993 |
| WO | WO 93/20877 | 10/1993 |
| WO | WO 94/04220 | 3/1994 |
| WO | WO 94/06510 | 3/1994 |
| WO | WO 94/10921 | 5/1994 |
| WO | WO 94/10924 | 5/1994 |
| WO | WO 94/10925 | 5/1994 |
| WO | WO 94/23659 | 10/1994 |
| WO | WO 94/26228 | 11/1994 |
| WO | WO 94/28809 | 12/1994 |
| WO | WO 95/02369 | 1/1995 |
| WO | WO 95/05781 | 3/1995 |
| WO | WO 95/09576 | 4/1995 |
| WO | WO 95/09577 | 4/1995 |
| WO | WO 95/10320 | 4/1995 |
| WO | WO 95/10321 | 4/1995 |
| WO | WO 95/17855 | 7/1995 |
| WO | WO 95/18575 | 7/1995 |
| WO | WO 95/19733 | 7/1995 |
| WO | WO 95/20360 | 8/1995 |
| WO | WO 95/23558 | 9/1995 |
| WO | WO 95/24160 | 9/1995 |
| WO | WO 95/25472 | 9/1995 |
| WO | WO 95/26686 | 10/1995 |
| WO | WO 95/30377 | 11/1995 |
| WO | WO 95/31144 | 11/1995 |
| WO | WO 96/00036 | 1/1996 |
| WO | WO 96/00039 | 1/1996 |
| WO | WO 96/00040 | 1/1996 |
| WO | WO 96/00042 | 1/1996 |
| WO | WO 96/00043 | 1/1996 |
| WO | WO 96/00528 | 1/1996 |
| WO | WO 96/04859 | 2/1996 |
| WO | WO 96/07360 | 3/1996 |
| WO | WO 96/09010 | 3/1996 |
| WO | WO 96/10367 | 4/1996 |
| WO | WO 96/11638 | 4/1996 |
| WO | WO 96/14020 | 5/1996 |
| WO | WO 96/14021 | 5/1996 |
| WO | WO 96/18349 | 6/1996 |
| WO | WO 96/19152 | 6/1996 |
| WO | WO 96/23448 | 8/1996 |
| WO | WO 96/23449 | 8/1996 |
| WO | WO 96/24296 | 8/1996 |
| WO | WO 96/24301 | 8/1996 |
| WO | WO 96/27337 | 9/1996 |
| WO | WO 96/29946 | 10/1996 |
| WO | WO 96/32897 | 10/1996 |
| WO | WO 96/34567 | 11/1996 |
| WO | WO 96/34569 | 11/1996 |
| WO | WO 96/34570 | 11/1996 |
| WO | WO 96/34571 | 11/1996 |
| WO | WO 96/37146 | 11/1996 |
| WO | WO 96/38094 | 12/1996 |
| WO | WO 96/39085 | 12/1996 |
| WO | WO 96/39086 | 12/1996 |
| WO | WO 96/39088 | 12/1996 |
| WO | WO 96/39089 | 12/1996 |
| WO | WO 96/39966 | 12/1996 |
| WO | WO 96/39967 | 12/1996 |
| WO | WO 97/00646 | 1/1997 |
| WO | WO 97/00647 | 1/1997 |
| WO | PCT/GB97/00066 | 5/1997 |
| WO | WO 97/24993 | 7/1997 |
| WO | WO 97/38637 | 10/1997 |
| WO | WO 98/00070 | 1/1998 |
| WO | WO 98/14131 | 4/1998 |

OTHER PUBLICATIONS

Pearce, John A., *Electrosurgery*, John Wiley & Sons Inc., New York, 1986, pp. 17, 69–75 and 87.

Wyeth, G.A., *Electrosurgical Unit*, pp. 1180–1202.

Everest Medical Technologies, Inc., "Everest Bipolar Laparoscopic Cholecystectomy," Transcript of Lecture by Dr. Olsen, Oct. 7, 1991.

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies for Dissection in Endoscopic Surgery:Nd:YAG Laser, High Frequency and Water–Jet," End. Surg., vol. 2, 1994, pp. 195–201.

Newman, Laura, "Could Twist on TURP Knock Lasers Out," Urology Times, vol. 3, No. 3, Mar. 1995, p. 21.

ArthroCare Corporation, "The Arthrocare Arthroscopic System," 1995.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology, vol. 146, Sep. 1991, pp. 669–674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., A Bipolar Electrosurgical TURP Loop, Abstract of Paper P14–11, 7$^{th}$ World Congress on Endourology and ESWL, Nov. 27–30, Kyoto, Japan, 1989, p. 248.

Ramsay, J.W. A. et al., "A Comparison of Bipolar and Monopolar Diathermy Probes in Experimental Animals," Urological Research, Springer–Verlag 1985, 13:99–102.

German Article w/ Translation: Elsasser, E. and Roos, E., "Concerning an Instrument for Transurethral Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp. 42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–1386.

Lee, Benjamin I. et al., "Thermal Compression and Molding of Atherosclerotic Vascular Tissue with Use of Radiofrequency Energy: Implications for Radiofrequency Balloon Angioplasty," Journal of American College of Cardiology, vol. 13, No. 5, Apr. 1989, pp. 1167–1175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulation: Bipolar vs. Monopolar in the Treatment of Experimental Canine Gastric Ulcer Bleeding," Gastroenterology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Sciences, vol. 26, No. 7, Jul. Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A. J., "The Bovie Electrosurgical Current Generator—Some Underlying Principles and Results," Archives of Surgery, vol. 18, 1929, pp. 1863–1873.

McLean, A. J., "Characteristics of Adequate Electrosurgical Current," American Journal of Surgery, vol. XVIII, No. 3, Feb. 16, 1932, pp. 417–441.

Wattiez, Arnaud et al., *Electrosurgery in Operative Endoscopy*, Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery," End. Surg. 1993, pp. 85–90.

Penketh, Richard et al., "Clinical Evaluation of the Procision Bipolar Electrosurgical Generator During Laparoscopic Gynaecological Procedures," EAES, 2$^{nd}$ International Congress of the European Association for Endoscopic Surgery, Madrid, Sep. 15–17, 1994.

Lloyd, David M. et al., "A New Portable Bipolar Generator–Use in Laparoscopic Cholecystectomy," EAES, 2$^{nd}$ International Congress of the European Association for Endoscopic Surgery, Madrid, Sep. 15–17, 1994.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986, pp. 559–565.

Pearce, John A., "Chapter 3 Electrosurgery," *Handbook of Biomedical Engineering*, Ed. Jacob Kline, Academic Press, Inc., 1988, pp. 99–113.

Selikowitz, Stuart M. et al., "Electric Current and Voltage Recordings on the Myocardium During Electrosurgical Procedures in Canines," *Reprint from Surgery, Gynecology & Obstetrics*, Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol. 159, pp. 39–43.

Lu, David Y. et al., "Electrical Thermal Angioplasty: Catheter Design Features, In Vitro Tissue Ablation Studies and In Vivo Experimental Findings," Am J Cardiol, vol. 60, 1987, pp. 1117–1122.

Malis, Leonard I., "Electrosurgery: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., *Medical Device Accidents—With Illustrative Cases*, CRC Press, New York, 1998, p. 93 (commentary on Honig, William M., "The Mechanism of Cutting in Electrosurgery," IEEE Transactions on Biomedical Engineering, Jan. 1975, pp. 58–65).

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bipolar Electrosurgery, pp. 1–4.

Description of Codman and Johnson & Johnson Malis CMC–III Bipolar System.

Pfizer/Valleylab Press Release "Valleylab Inc. Introduces The Procision Bipolar Electrosurgery System," Sep. 15, 1994.

ArthroCare Corporation, "ArthroCare Arthroscopic Electrosurgery System, Model 970 Operator's Manual," Feb. 1996.

ArthroCare Corporation, "Arthroscopic Electrosurgery System, System 2000 Operator's Manual," Jan. 1998.

* cited by examiner

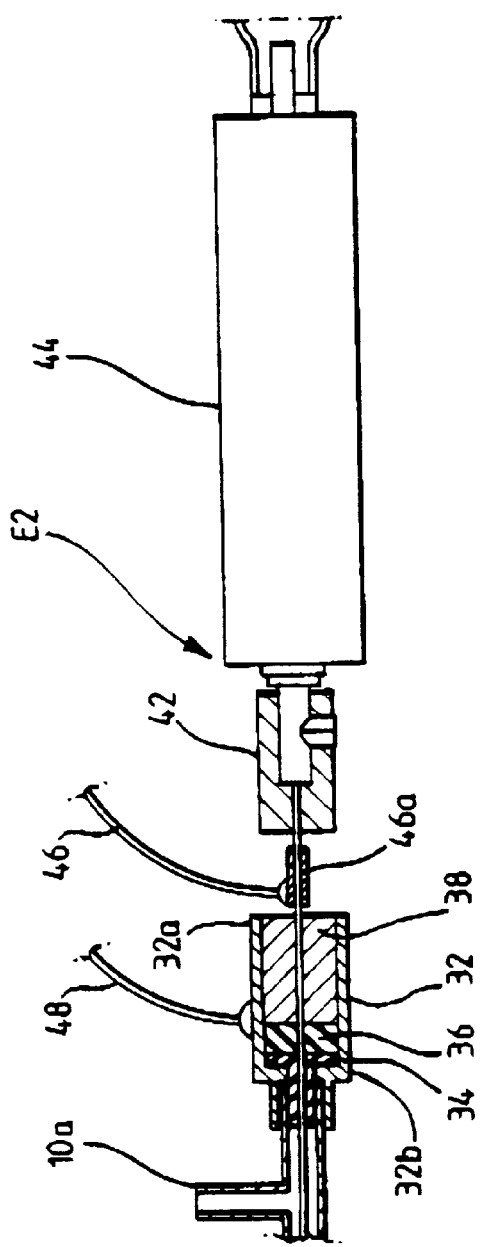
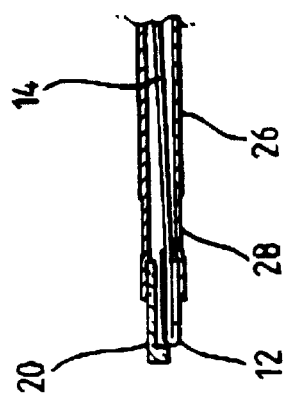
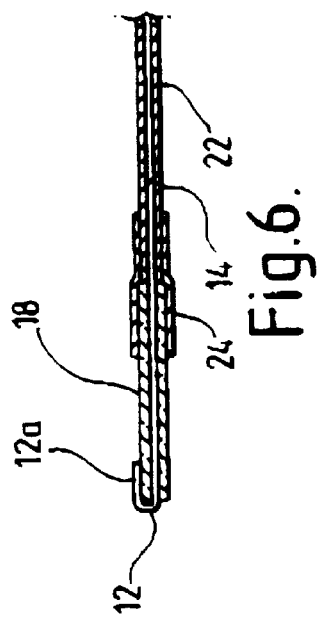
Fig.5.
Fig.6.

ELECTROSURGICAL INSTRUMENT

This application is a continuation-in-part of U.S. application Ser. No. 09/115,675, filed on Jul. 15, 1998 and now abandoned, a continuation-in-part of U.S. application Ser. No. 09/462,926, filed on Jan. 18, 2000, which is the U.S. National Phase Application of International Application No. PCT/GB98/02081, filed Jul. 15, 1998, and a continuation-in-part of U.S. application Ser. No. 09/202,025, filed on Dec. 8, 1998, which is the U.S. National Phase Application of International Application No. PCT/GB97/01632, filed Jun. 17, 1997.

This invention relates to an electrosurgical instrument for the treatment of tissue in the presence of an electrically-conductive fluid medium, to electrosurgical apparatus including such an instrument, and to an electrode unit for use in such an instrument. Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characterised as resectoscopes, are generally employed when the body cavity may be accessed through a natural body opening—such as the cervical canal to access the endometrial cavity of the uterus, or the urethra to access the prostate gland and the bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and the output power. Spacing the electrodes further apart would often obscure vision of the application site, and would require a modification in surgical technique to ensure direct contact of both electrodes with the tissue.

There are a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1:1 to avoid differential electrical stresses occurring at the contact between the tissue and the electrode.

The electrical junction between the return electrode and tissue can be supported by wetting of the tissue by a conductive solution such as normal saline. This ensures that the surgical effect is limited to the active electrode, with the electric circuit between the two electrodes being completed by the tissue. One of the obvious limitations with the design is that the active electrode (typically a needle) must be completely buried in the tissue to enable the return electrode to complete the circuit. Another problem is one of the orientation: even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intra-vascular absorption occurs. In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v; 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided.

Carbon dioxide is the preferred gaseous distension medium, primarily because of its non-toxic nature and high water solubility.

In endoscopic procedures in which the distension medium is a gas, the applicants have found that it is possible to use an electrically-conductive gas (such as argon) in place of carbon dioxide. Argon is conductive when excited into a discharge state, and has been employed in both endoscopic and conventional monopolar electrosurgery as a method of increasing the distance between the tissue and the instrument, by providing a conductive path between the two when high voltage electrosurgical outputs such as spray or fulgurate are being used. The high voltages used in this application result in a very low penetration of the electrosurgical effect into the tissue, making the technique only suitable to control bleeding from multiple small blood vessels. This allows the surgeon to staunch bleeding from multiple sites in a surgical sites in a surgical wound using a rapid "painting" technique, rather than applying electrosurgery to each individual bleeding site. The argon gas is delivered through a hollow surgical instrument, and passes over the monopolar electrode exposed at the tip of the instrument as a stream. This produces a region at the operative site which is rich in argon, and which contributes to the distension of the body cavity. High voltage monopolar electrosurgical outputs are undesirable in endoscopic surgery, because of the risks of damaging structures outside the field of vision, by either capacitive or direct coupling to a portion of the instrument remote from the operative site often outside the field of vision of the operator.

The applicants have developed a bipolar instrument suitable for underwater electrosurgery using a conductive liquid or gaseous medium. This electrosurgical instrument for the treatment of tissue in the presence of a fluid medium, comprises an instrument body having a handpiece and an instrument shaft and an electrode assembly, at one end of the shaft. The electrode assembly comprises a tissue treatment (active) electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the return electrode, being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of our International Patent Application No. PCT/GB96/01473 (the contents of which are hereby incorporated by reference).

The electrode structure of this instrument, in combination with an electrically-conductive fluid medium largely avoids the problems experienced with monopolar or bipolar electrosurgery. In particular, input power levels are much lower than those generally necessary with a monopolar arrangement (typically 100 watts). Moreover, because of the relatively large spacing between its electrodes, an improved depth of effect is obtained compared with conventional bipolar arrangements.

The specification of our International Patent Application No. GB96/01472 describes an irrigated bipolar electrosurgical instrument that can be used in open air or gas-filled environments. This instrument includes an internal channel for feeding electrically-conductive fluid (typically saline) to the exposed end of a tissue treatment electrode so as to provide a conductive fluid path that completes an electrical circuit to a return electrode when the instrument is in use. This instrument also includes an internal channel for removing fluid from the region of the exposed end of the tissue treatment electrode. When the fluid is a liquid, such as saline, the presence of that liquid can cause collateral tissue damage, so its removal is desirable. This type of instrument is intended primarily for use in open air or gas-filled environments, and is not suitable for use with electrosurgical procedures which require distension of a body cavity.

However, where the volume of a body cavity is small—for example in arthroscopic surgery where even the large joints, such as the knee, may only accommodate 50–60 ml of irrigation fluid—the following problems may occur, namely:

(i) Heated fluid in the immediate vicinity of the tissue contact electrode can cause collateral tissue damage;

(ii) The products of the tissue vaporised by the tissue contact electrode can cause visualisation problems; and (iii) Soft tissue present in a joint space tends to move about, making it difficult to apply the active electrode to vaporise such tissue.

An arthroscope electrode may be characterised as short (100 to 140 mm), and rigid with a working diameter up to 5 mm. It can be introduced through a stab incision into a joint cavity (with or without a cannula) using the triangulation technique. Such an electrode is operated with a motion which moves the electrode between the 9 O'Clock and 3 O'Clock positions on the arthroscopic image. As a result, the tissue to be treated is usually approached at a shallow working angle with respect to the axis of the electrode. An arthroscopic electrode thus needs to have an effect consistent with this angled approach to the tissue. The tissue to be treated, such as meniscal cartilage, is commonly dense and of a high electrical impedance. An arthroscope electrode requires output power and voltage settings that reflect the type of tissue being treated, the size of electrode, and the fact that arthroscopists are seeking a speed of effect comparable to that of the mechanical shaver devices they currently employ, albeit with an electrode of smaller dimensions than a shaver blade for improved access. The specification of our British Patent Application 9612993.7 (the contents of which are hereby incorporated by reference) describes an electrosurgical instrument for the treatment of tissue in the presence of an electrically-conductive fluid medium. The instrument comprises an instrument shaft, and an electrode assembly at one end of the shaft, the electrode assembly comprising a tissue treatment electrode and a return electrode which is electrically insulated from the tissue treatment electrode by means of an insulation member. The tissue treatment electrode has an exposed end for treating tissue, and the return electrode has a fluid contact surface which is spaced from the tissue treatment electrode in such a manner as to define, in use, a conductive fluid path that completes an electrical circuit between the tissue treatment electrode and the return electrode. The electrode assembly is provided with a plurality of apertures in the region of the tissue treatment electrode, through which apertures vapour bubbles and/or particulate material can be aspirated from the region surrounding the tissue treatment electrode.

An RF generator is provided for powering the electrode assembly. The power required from the RF generator to achieve vaporisation depends on a number of variables more fully described in the specification of our International Patent Application No. GB97/00065 (the contents of which are hereby incorporated by reference). Of these variables two, are of particular importance in the context of the present invention; one being the cooling effect produced by the aspiration of conductive fluid in the region of the tissue contact electrode, and the other being the disruption of the vapour pocket formed around the tissue contact electrode by the flow of conductive fluid. These problems can be partially overcome by coordinating the aspiration by monitoring the output features of the generator which indicate the vaporisation power threshold has been exceeded. This usually results in a series of suction pulses as the vaporisation threshold is repeatedly exceeded between pulses and then elevated during the suction pulses so that, should vaporisation be maintained, the suction will be applied continuously. By using this technique, heated saline in the vicinity of the tissue contact electrode and vaporisation products can be successfully removed. The other desirable feature is the aspiration of loose tissue towards the tissue contact electrode, so that it can be stabilised during vaporisation. Whilst this can be achieved according to this technique; there are two significant performance limitations.

The first of these limitations is that the gaseous products of tissue vaporisation contain fatty products which have a sublimation property, i.e. they condense directly to a solid; sublimation occurring at temperatures well above boiling point. As the electrode shaft within the body cavity is cooled by the surrounding saline, these products are easily condensed. Thus, if a parallel suction shaft is used, the build up is along its entire length, and eventually completely blocks the tube. This process, even at the flow rates dictated by minimal influence on the power threshold, can cause very rapid blocking. For example, it is found that, with a moderately large electrode tip, using a 1 mm internal diameter suction tube, complete blockage occurs after 30 seconds of activation. Obviously, a larger tube bore would increase the time before blockage, but this occurs so rapidly that the required bore size for a useful electrode life is beyond the dimensions of the maximum shaft diameter. The problems of sublimation are compounded by aspiration of tissue pieces which are incompletely vaporised before being excised from the remainder of the tissue. Given the need to attract tissue and, therefore, the requirement for a strong suction pressure which, once tissue is engaged with the tissue contact electrode and the vaporisation threshold is continually exceeded by cessation of flow, increases the propensity for aspiration of unvaporised tissue and blockage of the aspiration channel.

The second of these limitations also relates to adherence of tissue to the tissue contact electrode. As indicated above, once the tissue obstructs flow, the vaporisation power threshold is exceeded, and suction is continuously applied. Under these circumstances, and particularly when aspiration channels are provided adjacent to the tissue treatment electrode, a steady state can be reached wherein the tissue is held around the periphery of the tissue contact electrode, the portion of tissue in the immediate vicinity of the tissue treatment electrode is vaporised but, without moving the application site or redirecting suction solely through the tissue treatment electrode, no further removal of tissue will occur. For example, large pieces of tissue tend to bridge the tissue treatment electrode, so that all tissue in contact with the electrode is removed, but the bulk of the tissue is left in place. Applying suction solely through the tissue treatment electrode limits the size of the electrode otherwise two extremes are created where, on the one hand during activation in conductive fluid, the vaporisation power threshold is very elevated despite synchronising suction pulses with the RF output, typically >200 Watts, yet, on the other hand, can be reduced to below 50% of this level once tissue is engaged. With a static tissue contact electrode, there is an inevitable compromise between these performances variables.

One aim of the invention to provide an improved electrosurgical instrument of this type.

A first aspect of the present invention provides an electrosurgical instrument for the treatment of tissue in the presence of an electrically-conductive fluid medium, the instrument comprising an instrument shaft, and a tissue treatment electrode mounted at the distal end of the shaft for electrosurgically excising tissue pieces at an operation site, the tissue treatment electrode being movable cyclically relative to the distal end of the shaft, wherein vaporisation threshold control means are provided for controlling the power threshold for vaporisation of the electrically-conductive fluid medium at the tissue treatment electrode.

Preferably, the instrument further comprises drive means for moving the tissue treatment electrode relative to the distal end of the shaft.

Advantageously, the instrument further comprises a return electrode which is electrically insulated from the tissue treatment electrode by insulation means, the tissue treatment electrode being exposed at the distal end of the instrument, and the return electrode having a fluid contact surface spaced proximally from the exposed end of the tissue treatment electrode.

In a preferred embodiment, the tissue treatment electrode is movable cyclically relative to the return electrode so as to move the tissue treatment electrode cyclically into, and out of, at least one position in which arcing occurs between the tissue treatment and return electrodes.

Advantageously, the tissue treatment electrode is provided at the distal end of a rod mounted within, and movable relative to, the instrument shaft. Conveniently, the tissue treatment electrode is constituted by the distal end portion of the rod.

In a preferred embodiment, the drive means is such as to reciprocate the rod within the channel. Advantageously, the drive means is constituted by a motor and coupling means for converting the rotary output of the motor into reciprocatory movement of the rod.

In another preferred embodiment, the drive means is such as to rotate the rod within the channel. An electric motor may constitute the drive means.

In yet another preferred embodiment, the control means is such as to produce turbulence in the fluid medium surrounding the tissue treatment electrode, whereby, should vaporisation of the fluid medium surrounding the tissue treatment electrode cease, the control means is effective to reduce the turbulence, thereby to allow vaporisation to be re-established.

Preferably, the control means is such as to vary the rate of cyclical movement of the tissue treatment electrode thereby producing said turbulence in the fluid medium surrounding the tissue treatment electrode.

The instrument may further comprise removal means, the instrument having an apertured portion through which matter can be aspirated by the removal means from the region surrounding the tissue treatment electrode, the removal means comprising a channel formed within the instrument shaft and leading from the apertured portion.

Preferably, the removal means further comprises a pump connected to the channel at a region thereof remote from the apertured portion of the instrument. In this case, the control means may be such as to vary the rate of the pump thereby producing said turbulence in the fluid medium surrounding the tissue treatment electrode. In this case, the pump may be activated cyclically whereby matter is aspirated by the removal means in a pulsed fashion. Conveniently, the pump is activated only when the tissue treatment electrode is powered for tissue vaporisation.

The instrument may further comprise an RF generator having a bipolar output connected to the tissue treatment electrode and the return electrode. Advantageously, the RF generator supplies energy to the drive means. Preferably, the control means includes a vaporisation detection circuit for detecting vaporisation in the region of the tissue treatment electrode, the vaporisation detection circuit being connected to the output of the RF generator whereby the vaporisation power threshold is controlled in dependence upon the output characteristics of the RF generator.

The control means may further include an RF active detection circuit for detecting the presence of RF voltages at the output of the RF generator, whereby the pump can be activated before the RF generator is turned on.

A further independent aspect of the present invention provides an electrosurgical instrument for the treatment of tissue in the presence of an electrically-conductive fluid medium, the instrument comprising an instrument shaft, a tissue treatment electrode mounted at the distal end of the shaft for electrosurgically excising tissue pieces at an operation site, morcellation means for electrosurgically reducing the size of excised tissue pieces, and removal means for removing morcellated tissue pieces, the instrument having an apertured portion through which matter can be aspirated by the removal means from the region surrounding the tissue treatment electrode, the removal means comprising a channel formed within the instrument shaft and leading from the apertured portion, wherein the tissue treatment electrode is movable cyclically relative to the distal end of the shaft, and constitutes the morcellation means.

Preferably, the instrument further comprises drive means for moving the tissue treatment electrode relative to the distal end of the shaft.

Morcellation is the division of a tissue piece into many smaller pieces in order to facilitate its surgical removal.

Advantageously, the instrument further comprises a return electrode which is electrically insulated from the tissue treatment electrode by insulation means, the tissue treatment electrode being exposed at the distal end of the instrument, and the return electrode having a fluid contact surface spaced proximally from the exposed end of the tissue treatment electrode.

In a preferred embodiment, the tissue treatment electrode is movable cyclically relative to the return electrode so as to move the tissue treatment electrode cyclically into, and out of, at lest one position in which arcing occurs between the tissue treatment and return electrodes.

Preferably, the channel is defined by the instrument shaft.

Conveniently, the tissue treatment electrode is provided at the distal end of a rod mounted within, and moveable relative to, the instrument shaft. Thus, movement of the rod results in movement of the tissue treatment electrode, and this prevents tissue bridging, as the tendency for tissue to obstruct the channel is obviated by the electrode movement ensuring that such tissue is treated. Tissue can, therefore, be electrosurgically removed from an operation site by a vaporisation technique, and can be electrosurgically morcellated in this region by the moving tissue treatment electrode, this process being analogous to a miniature liquidiser. Preferably, the tissue treatment electrode is constituted by the distal end portion of the rod.

Advantageously, the rod is constituted by a tungsten wire having a diameter in the range from 0.2 mm to 1.0 mm. Preferably, the tungsten wire has a diameter in the range from 0.4 mm to 0.6 mm.

Advantageously, the tissue treatment electrode is angled with respect to the longitudinal axis of the instrument shaft, and the instrument further comprises an insulating sleeve surrounding the rod proximally of said angled end portion. The insulating sleeve may be a ceramic sleeve.

Preferably, the insulation member is formed with a slot which constitutes the apertured portion, the tissue treatment electrode passing through the slot. Alternatively, the apertured portion is constituted by a gap between the tissue treatment electrode and the insulation member.

In a preferred embodiment, the drive means is such as to reciprocate the rod within the channel. Advantageously, the drive means is constituted by a motor and coupling means for converting the rotary output of the motor into reciprocatory movement of the rod.

In this case, the angled end portion of the rod may be at right angles to the longitudinal axis of the instrument shaft, and the tip of the angled end portion may constitute the tissue contacting portion of the tissue treatment electrode. This electrode is, therefore, a side effect electrode.

In another preferred embodiment, the drive means is such as to rotate the rod within the channel. An electric motor may constitute the drive means.

Advantageously, the angled end portion of the rod is at right angles to the longitudinal axis of the instrument shaft, and the distal end surface of said angled end portion constitutes the tissue contacting end portion of the tissue treatment electrode. The rotation of the angled end portion of the rod permits the use of a small diameter rod, and hence the use of a small tissue treatment electrode, whilst providing a relatively large area tissue contacting position. The use of a small diameter tissue treatment electrode also permits the use of lower electrosurgical powers an/or higher fluid medium flow rates.

Alternatively, the angled end portion of the rod makes an acute angle with the longitudinal axis of the instrument shaft, and the insulation member is provided with an inclined cam surface which is engageable with the apex of the angled end portion of the rod.

It is also possible for the angled end portion of the rod to be bent back around the distal end portion of the insulating sleeve.

Preferably, the removal means further comprises a pump connected to the channel at a region thereof remote from the apertured portion of the instrument. The pump may be activated cyclically whereby matter is aspirated by the removal means in a pulsed fashion. Conveniently, the pump is activated only when the tissue treatment electrode is powered for tissue vaporisation.

The instrument may further comprise an RF generator having a bipolar output connected to the tissue treatment electrode and the return electrode. Advantageously, the RF generator supplies energy to the drive means. Preferably, the pump is controlled in dependence upon the output characteristics of the RF generator.

Yet a further independent aspect of the present invention provides a electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed end for treating tissue, and the return electrode having a fluid contact surface which is spaced proximally from the tissue treatment electrode in such a manner as to define, in use, a conductive fluid path that completes an electrical circuit between the tissue treatment electrode and the return electrode, wherein the electrode assembly is provided with a plurality of apertures in the region of the tissue treatment electrode and distal to the return electrode, through which apertures vapour bubbles and/or particulate material can be aspirated from the region surrounding the tissue treatment electrode.

In a preferred embodiment, the instrument further comprises a pump for subjecting the distal end portion of the instrument shaft to a sub-atmospheric pressure thereby to aspirate, in use, vapour bubbles and/or particulate material through said apertures from the region surrounding the tissue treatment electrode.

Advantageously, the pump is activated cyclically whereby matter is aspirated in a pulsed fashion. The pump may additionally or alternatively be activated only when the tissue treatment electrode is powered for tissue vaporisation.

Preferably, the instrument further comprises an RF generator having a bipolar output connected to the tissue treatment electrode and the return electrode. In this case, the pump may be controlled in dependence upon the voltage output characteristics of the RF generator. In this way, the flow of vapour bubbles and/or aspirated particulate material is balanced to the voltage output characteristics of the RF generator to prevent excessive cooling of the tissue treatment electrode and a resultant increase in the vaporisation power threshold.

The return electrode is spaced from the tissue treatment electrode so that, in use, it does not contact the tissue to be treated, and so that the electrical circuit is always completed by the conductive fluid, and not simply by arcing between the electrodes. Indeed, the arrangement is such that arcing between adjacent parts of the electrode assembly is avoided, thereby ensuring that the tissue treatment electrode can become enveloped in a vapour pocket so that tissue entering the vapour pocket becomes the preferred path for current to flow back to the return electrode via the conductive fluid.

The electrosurgical instruments of the invention are useful for dissection, resection, vaporisation, desiccation and coagulation of tissue, as well as for combinations of these functions. They have a particular application in arthroscopic surgery as it pertains to endoscopic and percutaneous procedures performed on joints of the body including, but not limited to, such techniques as they apply to the spine and other non-synovial joints. Arthroscopic operative procedures may include: partial or complete meniscectomy of the knee joint including meniscal cystectomy; lateral retinacular release of the knee joint; removal of anterior and posterior cruciate ligaments or remnants thereof; labral tear resection, acromioplasty, bursectomy and subacromial decompression of the shoulder joint; anterior release of the temperomandibular joint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body; discectomy either in the treatment of a disc prolapse or as part of a spinal fusion via a posterior or anterior approach to the cervical, thoracic and lumbar spine or any other fibrous joint for similar purposes; excision of diseased tissue; and haemostasis.

The instruments of the invention are also useful for dissection, resection, vaporisation, desiccation and coagulation of tissue, as well as combinations of these functions, with particular application in urological endoscopic (urethroscopy, cystoscopy, ureteroscopy and nephroscopy) and percutaneous surgery. Urological procedures may include: electro-vaporisation of the prostate gland (EVAP) and other variants of the procedure commonly referred to as transurethral resection of the prostate (TURP) including, but not limited to, interstitial ablation of the prostate gland by a percutaneous or perurethral route whether performed for benign or malignant disease; transurethral or percutaneous resection of urinary tract tumours as they may arise as primary or secondary neoplasms, and further as they may arise anywhere in the urological tract from the calyces of the kidney to the external urethral meatus; division of strictures as they may arise at the pelviureteric junction (PUJ), ureter, ureteral orifice, bladder neck or urethra; correction of ureterocoele; shrinkage of bladder diverticular; cystoplasty procedures as they pertain to corrections of voiding dysfunction; thermally induced shrinkage of the pelvic floor as a corrective treatment for bladder neck descent; excision of diseased tissue; and haemostasis.

The electrosurgical instruments of the invention are also useful for dissection, resection, vaporisation, desiccation and coagulation of tissue and combinations of these functions with particular application in laparascopic, colposcopic (including vaginal speculum) and open surgical procedures on the female genital tract and adnexal related diseases. Laparascopic operative procedures may include: removal of subserosal and pedunculated fibroids, ablation of ectopic endometrium, ovarian cystectomy and ovarian drilling procedures; oophorectomy, salpingo-oophorectomy, subtotal hysterectomy and laparaoscopically assisted vaginal hysterectomy (LAVH) as may be performed for benign or malignant diseases; laparoscopic uterosacral nerve ablation (LUNA); fallopian tube surgery as correction of ectopic pregnancy or complications arising from acquired obstructions; division of abdominal adhesions; and haemostasis.

The electrosurgical instruments of the invention are also useful in the lower female genital tract, including treatment of cervix, vagina and external genitalia whether accessed directly or using instrumentation comprising generally speculae and colposcopes. Such applications include: vaginal hysterectomy and other pelvic procedures utilising vaginal access; LLETZ/LEEP procedure (large loop excision of the transformation zone) or excision of the transformation zone of the endocervix; removal of cystic or septic lesions; ablation of genital or venereal warts; excision of benign and malignant lesions; cosmetic and surgical repairs including vaginal prolapse; excision of diseased tissue; and haemostasis.

The electrosurgical instruments of the invention are also useful for dissection, resection, vaporisation, desiccation and coagulation of tissue and combinations of these functions with particular application in surgery on the ear, nose and throat (ENT), and more particularly procedures performed on the oropharynx, nasopharynx and sinuses. These procedures may be performed through the mouth or nose using speculae or gags or using endoscopic techniques such as functional endoscopic sinus surgery (FESS). Functional endoscopic sinus procedures may include: removal of chronically-diseased inflamed and hypertrophic mucus linings, polyps and neoplasms from the various anatomical sinuses of the skull; excision of diseased tissue; and haemostasis. Procedures on the nasopharynx may include: removal of chronically-diseased inflamed and hypertrophic mucus linings, polyps and neoplasms from the turbinates and nasal passages; submucous resection of the nasal septum; excision of diseased tissue; and haemostasis. Procedures on the oropharynx may include: removal of chronically-diseased, inflamed and hypertrophic tissue, polyps and neoplasms particularly as they occur related to the tonsil, adenoid, epi-glottic and supra-glottic regions, and salivary glands; as an alternative method to perform the procedure commonly known as laser assisted uvolopalatoplasty (LAUP); excision of diseased tissue; and haemostasis.

It is evident from the scope of applications of the invention that it has further additional applications for dissection, resection, vaporisation, desiccation and coagulation of tissue and combinations of these functions in general laparoscopic, thoracscopic and neurosurgical procedures, being particularly useful in the removal of diseased tissue and neoplastic disease whether benign or malignant.

Surgical procedures using the electrosurgical instrument of the invention may also include introducing the electrode assembly to the surgical site, whether through an artificial conduit (a cannula) or a natural conduit, which may be in an anatomical body cavity or space, or one created surgically. The cavity or space may be distended during the procedure using a fluid, or may be naturally held open by anatomical structures. The surgical site may be bathed in a continuous flow of conductive fluid such as saline solution either to fill and distend the cavity, or to create a locally-irrigated environment around the tip of the electrode assembly in a gas filled cavity. The irrigating fluid may be aspirated from the surgical site to remove products created by application of the RF energy, tissue debris or blood. The procedures may include simultaneous viewing of the site via an endoscope, or using an indirect visualisation means. An irrigated bipolar electrosurgical instrument is described in the specification of our International Patent Application No. PCT/GB96/01472 (the contents of which are hereby incorporated by reference).

Embodiments of the invention will now be described in greater detail, by way of example with reference to the drawings, in which:

FIG. 5 is a diagrammatic side elevation, partially broken away, of a second form of electrode unit constructed in accordance with the invention;

FIG. 6 is a diagrammatic side elevation of the electrode assembly of the electrode unit of FIG. 5;

Figure 1:
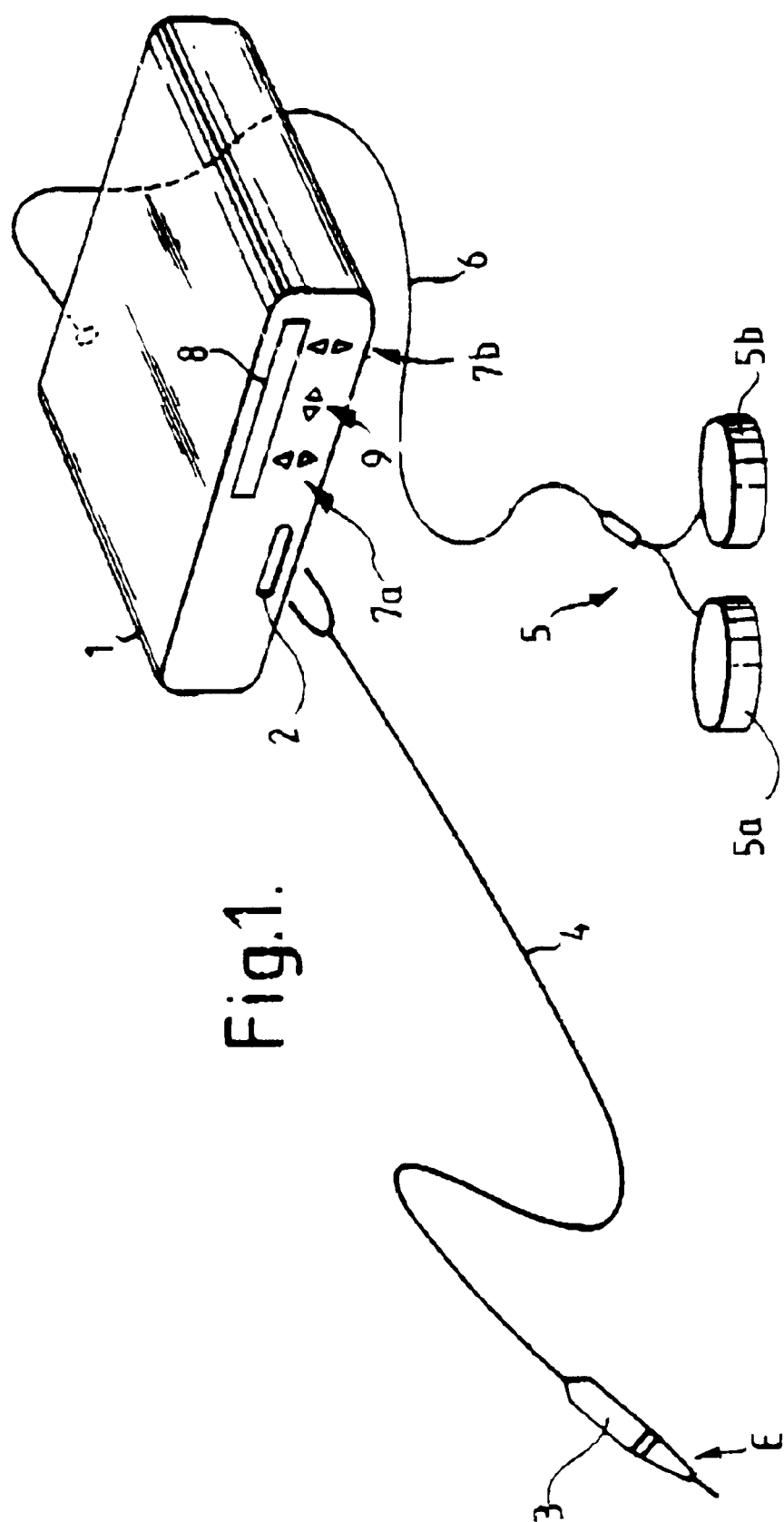
FIG. 1 is a diagram showing an electrosurgical apparatus constructed in accordance with the invention.

Referring to the drawings, FIG. 1 shows electrosurgical apparatus including a generator 1 having an output socket 2 providing a radio frequency (RF) output, via a connection cord 4, for an instrument in the form of a handpiece 3. Activation of the generator 1 may be performed from the handpiece 3 via a control connection (not shown) in the cord 4, or by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes.

The handpiece 3 mounts a detachable electrode unit E, such as the electrode units E1 and E4 to be described below.

Figure 2:
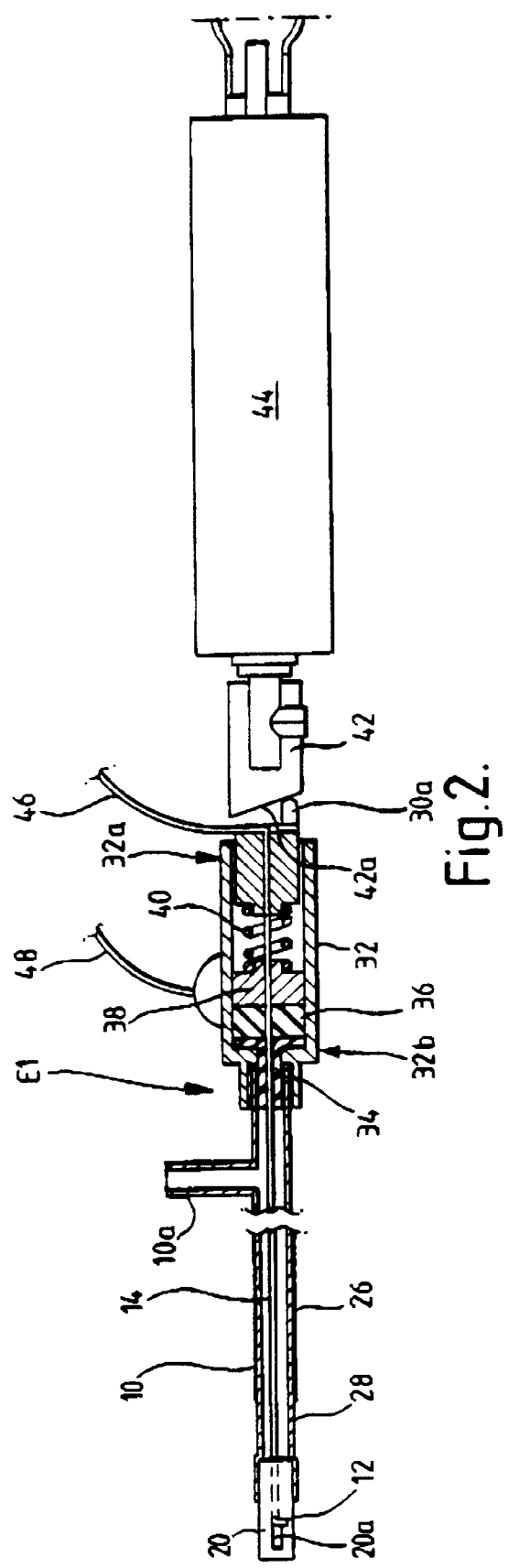
FIG. 2 is a diagrammatic side elevation, partially broken away, of a first form of electrode unit constructed in accordance with the invention.

FIG. 2 shows the first form of electrode unit E1 for detachable fastening to the electrosurgical instrument handpiece 3, the electrode unit comprising a shaft 10, which is constituted by a tube made of stainless steel. A tissue treatment (active) electrode 12 is provided at the distal end portion of the shaft 10. The active electrode 12 is provided by the distal end portion of a rod 14 made of tungsten, the active electrode extending at right angles to the rod. The rod 14 has a diameter of 0.4 to 0.6 mm. A ceramic tube 18 is fixed to the rod 14 immediately adjacent to the active electrode 12. A ceramic tip 20 is fixed within the out-turned distal end portion of the shaft 10.

As shown in FIG. 2, the active electrode 12 protrudes through a longitudinal slot 20a formed in the ceramic tip 20. That portion of the rod 14 not covered by the ceramic tube 18 is provided with an insulating sleeve 22 made of polyimide, polytetrafluoroethylene or by separate sleeves made by these two substances. A heat sleeve 24 made of polytetrafluoroethylene or polyimide, covers the adjoining regions of the ceramic tube 18 and the sleeve 22.

The major portion of the length of the shaft 10 is provided with an insulating heat shrink sleeve 26 made of polyvinylidenefluoride. The sleeve 26 does not cover the distal end portion of the shaft 10, that region of the shaft constituting a return electrode 28.

The rod 14 is mounted for reciprocal movement within the shaft 10, that end of the rod remote from the active electrode 12 being fixed to a coupling member 30 slidably mounted within one end 32a of a sleeve 32 made of stainless steel. The other end 32b of the sleeve 32 is fixed to the adjacent end portion of the shaft 10. A top hat washer 34 is located within the sleeve end 32b, the washer constituting a backing member for a silicone gland 36 and a delrin bush 38. A return spring 40 acts between the bush 38 and the coupling member 30. The rod 14 passes through apertures in the washer 34, the gland 36 and the bush 38.

An off-set shaft 30a is fixed to the end face of the coupling member 30, the free end of this shaft being engageable with an inclined end face 42a of a rotatable coupling member 42 fixed to the rotary output shaft of a motor 44. Hence, rotation of the output shaft of the motor 44 results in reciprocation of the coupling member 30 and the rod 14.

The hollow interior of the shaft 10 is connected to a transverse tubular member 10a which is connected to a suction pump (not shown), and so constitutes a suction/exhaust port. As shown in FIG. 2, the active electrode 12 is positioned at the end of an aspiration channel constituted by the annular cavity defined by the interior of the shaft 10 and the rod 14, so that vapour bubbles and/or particulate material which, in use, are formed in the region of the active electrode, can be aspirated from the region for removal via the slot 20a, the aspiration channel and the port 10a.

The RF generator 1 (not shown in FIG. 2) delivers an electrosurgical current to the electrodes 12 and 28 via connectors 46 and 48 provided respectively on the coupling member 30 and on the sleeve 32. The generator 1 includes means for varying the delivered output power to suit different electrosurgical requirements. Thus, in a first output power range of from about 140 volts to 200 volts, the active electrode 12 is used for tissue desiccation; and, in a second output power range of from about 250 volts to 600 volts, the active electrode is used for tissue removal by cutting or vaporisation. For both ranges, the voltages are peak voltages. The generator 1 may be as described in the specification of our European Patent Application 96304558.8.

This electrosurgical instrument is particularly useful for rapid tissue debulking and the removal of loose tissue. One of the problems which could be encountered when tissue is rapidly debulked using an arthroscopic electrode configuration, particularly when working in small joint spaces, is the production of vapour bubbles generated as an end product of tissue vaporisation. Such bubbles obscure vision, and can coalesce at the site of tissue application, so that the electrical circuit between the active and return electrodes becomes compromised by the absence of conductive fluid. Irregular active electrodes having filamentary, mesh or coiled spring forms goes some way to solving this problem as it reduces the vaporisation threshold as disclosed in the specification of our International patent application No. GB97/00065.

The provision of the suction pump ensures the elimination of vapour bubbles from an operation site, which is particularly advantageous during aggressive tissue debulking. The suction pump is activated only when the active electrode 12 is powered for tissue vaporisation. The pump is, therefore, pulsed so as to pull saline over the active electrode 12 (and to extract vapour bubbles and/or particulate material). This cools the active electrode 12, resulting in the collapse of the vapour pocket surrounding the active electrode. This, in turn, leads to the suction pump being turned off, thereby reducing the flow of saline over the active electrode 12. This electrode 12 then heats up again, leading to the re-formation of a vapour pocket, and the re-activation of the suction pump. This cycle then repeats until the generator 1 is turned off when the instrument is removed from the operation site.

The suction pump must be controlled so that the flow of bubbles from the active electrode 12 is balanced to the output characteristics of the RF generator 1 to prevent excessive cooling of the active electrode and a resultant increase in its vaporisation power threshold. The thermal mass of the thin, wire-form active electrode 12 is lower than that of a standard solid form active electrode, and this assists in rapidly re-establishing the vapour pocket around the active electrode should this collapse following excessive cooling.

The electrode unit E1 is intended primarily for use in arthroscopic surgery which requires rapid tissue debulking by vaporisation. The side-effect electrode (i.e. where the treatment axis is perpendicular to the shaft) configuration of the unit E1 is particularly advantageous for this purpose. In use, the electrosurgical instrument is manipulated to introduce the electrode assembly constituted by the active electrode 12 and the return electrode 28 into a selected operation site (e.g. within the joint space of a knee), so that the active electrode contacts the tissue to be treated, and the tissue and the electrode assembly are immersed in saline.

The footswitch 5b (or the push button 7b) is then operated to activate the generator 1. The generator 1 then provides sufficient RF power to the electrode assembly to vaporise the saline surrounding the active electrode 12, and to maintain a vapour pocket surrounding this electrode. Using a brushing technique, with firm pressure against the tissue surface, rapid debulking of the tissue is achieved. Gently touching the tissue will reduce the effect, and can be used to sculpture and smooth the residual tissue surface. With tissue engagement, the flow of irrigant away from the active electrode 12 will be reduced, the amount of reduction depending on the nature of the tissue surface, the application pressure and the suction pressure. Speed of debulking will, therefore, depend on these variables. Once the vaporisation occurs, the products will include vapour bubbles, carbon particles and tissue debris. All of these products are removed from the region of the active electrode 12, via the shaft 10 and the port 10a, by the suction pump.

All the constituents removed from the active tip are at high temperatures. This could lead to a potentially dangerous heating of the electrode shaft 10, which could cause tissue damage at the entry point. It may be, therefore, necessary to aspirate additional coolant saline from the body cavity along the inside surface of the shaft. To ensure that this saline is indeed at a safe temperature, it is taken from the rear of the return electrode 28 via a mesh filter (not shown).

In use, when the generator 1 is turned on, the motor 44 begins to rotate, causing the rod 14 to oscillate with an amplitude of 0.5 mm. The oscillation of the rod 14 within the shaft 10 provides a mechanical agitation within the shaft that is sufficient to dislodge any sublimation products which condense within the shaft. In this way, blockage of the shaft 10 is prevented, so that the instrument can be used on a continuous basis.

The oscillation of the active electrode 12 also ensures that tissue pieces removed electrosurgically by vaporisation from an operation side are morcellated electrosurgically by the oscillating electrode, thereby preventing large tissue pieces bridging the aspiration channel. Morcellation is the division of a tissue piece into many smaller pieces in order to facilitate its surgical removal.

The electrode unit E1 is also very effective in removing heated saline (distension fluid) from within a joint cavity. The risk of hot distension fluid occurs primarily during power application to reach the vaporisation threshold. Once the threshold has been reached, the power requirement falls by 30–50%.

Whilst aspiration from the region of the active electrode 12 will remove heated saline from the body cavity, and remove any risk of overheating through prolonged activation under conditions where the vaporisation threshold is not reached, the cooling effect and disruption of vapour pockets created around the active electrode will increase the vaporisation threshold. A vicious cycle can, therefore, be created, wherein the more suction applied at the active electrode 12, the more power required to reach the vaporisation threshold, and the greater the risk of heating. The other factor influencing the vaporisation threshold is the ratio of return: active contact area, and the insulation separation between the active electrode 12 and the return electrode 28. The size of the active electrode 12 and the insulation separation, should, therefore, be reduced to the minimum necessary to achieve the function in order to offset the effects of aspiration in elevating the power threshold of vaporisation.

The specification of our International Patent Application GB97/00065 discloses techniques for controlling the vaporisation threshold by employing active electrode designs which assist in capturing vapour pockets and preventing cooling of the active electrode application site by screening from the flow of irrigant provided by channels in an endoscope. An alternative method of reducing the vaporisation power threshold is to pulse the suction pressure, thereby allowing the threshold to be attained between pulses. Such pulses may be synchronised with the output features of the RF generator 1 to provide power bursts during active suction to sustain the vapour pocket, and clear any tissue occluding the apertures in the active electrode 12.

A known technique in arthroscopic surgery is to apply suction through a mechanical, tissue-nibbling device so that soft tissue present in the joint space, such as the infrapatellar fat pad, can be held in position within the nibbler jaws by suction whilst it is progressively "nibbled away".

Attracting tissue to the active electrode 12 of the electrode unit E1 has a similar effect as, for the reasons already given above, compliant tissue adhering to the active electrode will result in a reduction of the vaporisation power threshold. Adherent tissue will be rapidly vaporised, and small tissue particles produced during vaporisation will be aspirated from the application site.

Because of its speed of debulking and side-effect configuration, the electrode unit E1 also has advantages in urological surgery as an EVAP technique for use in conjunction with a resectoscope. A resectoscope electrode unit is introduced very differently, in that is mounted on an endoscope prior to passage of the assembled instrument through a working sheath via the urethra. The proximal end of the electrode unit is connected to a trigger assembly and an electrical contact which is integral with the resectoscope. By this means, the electrode unit E1 can be moved back and forth through a defined range of motion by operating the trigger mechanism. As the electrode unit E1 is assembled prior to introduction, the size of the tip is not constrained by working channel dimensions, but rather by the diameter of the working sheath which can be up to 10 mm. Part of this diameter is occupied by the support wires to the electrode unit E1, which wires are commonly bent in a downward angle, with respect to the endoscopic image, to the working tip, so that they do not interfere with either visulation or its operation. Because of the reciprocatory movement of the rod 14, the active electrode 12 operates over a length lying within the range of from 3 mm to 4 mm and a width lying in the range of from 2 mm to 3 mm, and this size is necessary for urological surgery given that, on average, 20–30 grammes of prostate tissue must be removed.

Because of the reservoir effect of the urinary bladder, and the mounting of the endoscope to view the tip of the active electrode 12 from below, bubble generation during vaporisation is less of a problem during endoscopic urology, as the bubbles flow away from the endoscope to accumulate in the bladder. Nevertheless, the use of the electrode unit E1 substantially reduces the possibility of bubble generation causing problems.

Although the electrode unit E1 is intended primarily for use in the vaporisation of tissue it can also be used for desiccation, particularly of synovial membranes or to separate muscle attachments. In this case, once the electrode assembly of the electrode unit E1 has been introduced into a selected operation site, the RF generator 1 is actuated using the footswitch 5a or the push button 7a. The generator 1 will then provide sufficient RF power to the electrode assembly to maintain the saline adjacent to the active electrode 12 substantially at its boiling point without creating a vapour pocket surrounding that electrode. The instrument can then be manipulated by moving the active electrode 12 across the surface of the tissue to be treated in a side-to-side "painting" technique.

The electrode unit E1 can also be used for delivering a blended power output. This is achieved by automatically alternating the output of the RF generator 1 between the desiccation and vaporisation power levels, more haemostasis being produced then is possible in the vaporisation mode. As a consequence, the speed of tissue debulking is reduced, but the increased haemostasis is useful when cutting or debulking vascular tissue structures. Alternatively, the output of the RF generator 1 can be pulsed at the vaporisation power level, without cycled activation of the desiccation mode. This produces a less aggressive tissue vaporisation than occurs in the vaporisation mode, with a consequent reduction in both bubble formation and the risk of tissue charring.

The active electrode 12 of the unit E1 is a side effect electrode (i.e. its treatment axis is perpendicular to the shaft). Axial agitation is advantageous with such electrodes, in that the entire electrode can be brought into contact with tissue. As a result, the exposed area can be made very small, allowing operation at lower powers and less at higher saline flow rates.

Reference above has been made to pulsing the operation of the suction pump to control the vaporisation power threshold at the active electrode 12. It is also possible to influence the vaporisation power threshold by reciprocating the electrode 12 so as to produce turbulence in the surrounding saline solution, the reciprocation speed being controlled or being pulsed depending on the degree to which the vaporisation power threshold is to be altered.

Figure 4:
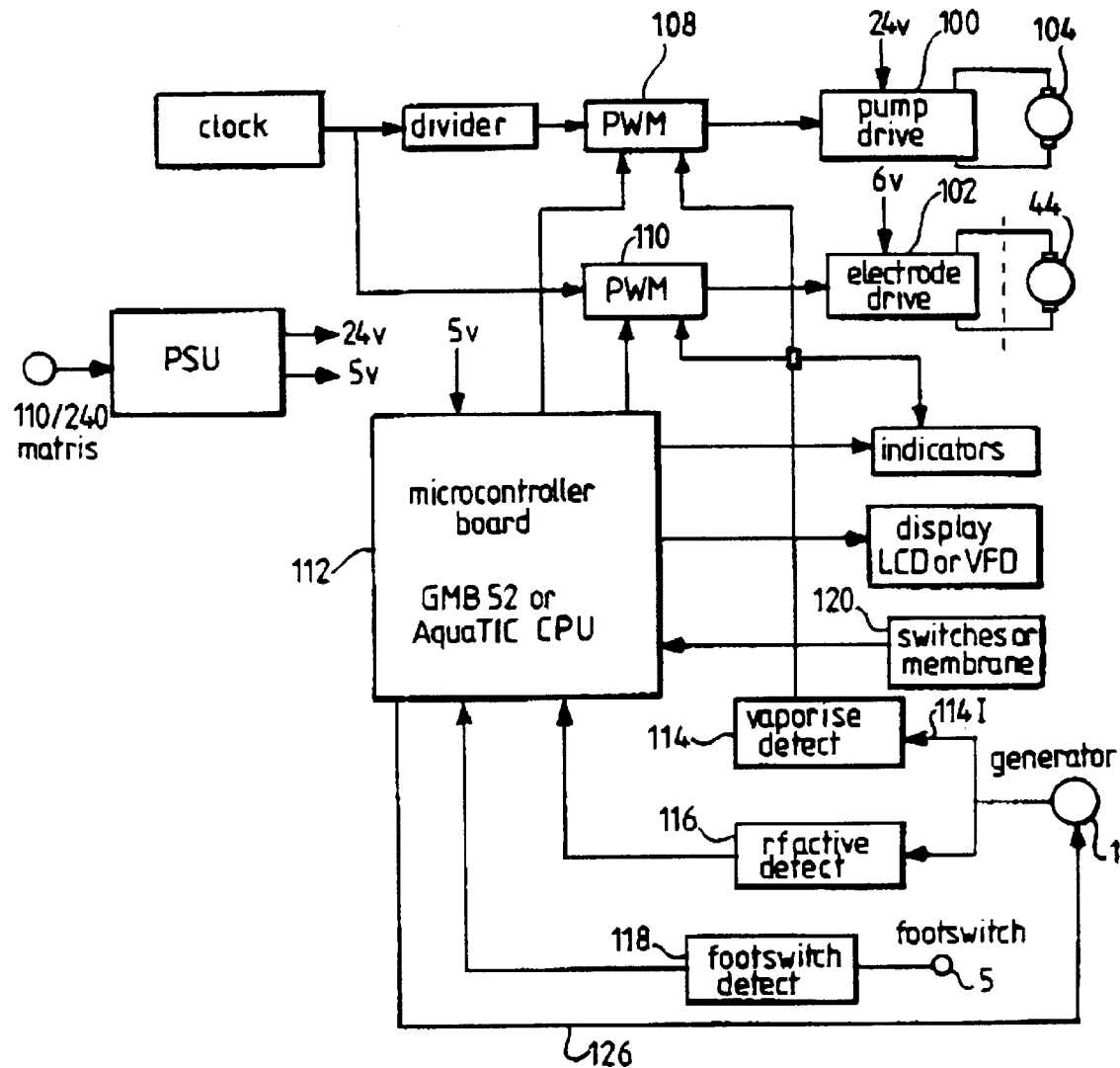
FIG. 4 is a block circuit diagram illustrating vaporisation power threshold control of the electrode unit of FIGS. 2 and 3.

Referring to FIG. 4, an electronic controller for achieving either power vaporisation threshold control function has a drive unit 100 for driving a pump motor 104, and a drive unit 102 for driving the motor 44 in response to variable pulse width modulation inputs derived from pulse width modulation circuits 108, 110. Both modulation circuits are controllable by a microcontroller 112 and a vaporisation detection circuit 114. The microcontroller 112 is, itself, under the control of an RF output active detection circuit 116 and a footswitch detection circuit 118. The maximum speeds of the two motors 104, 44 are user selected using switches 120, and are used to set up pulse width modulation pulse trains in each case by means of the respective circuit 108,110. However, the pulse widths from each circuit 108,110 are also controlled by the vaporisation detection circuit 114. The circuit has an input 114I connected to the output of the RF generator 1, and contains peak voltage sensing components as disclosed in our European Patent Application No. 0754437. When vaporisation at the electrode 12 occurs, the electrode peak voltage rises rapidly. When vaporisation at the electrode 12 occurs, the electrode peak voltages rises rapidly. Detection of this rise by the vaporisation detection circuit 114 causes the mark-to-space ratio of the signals fed to the motor drive circuits 100, 102 to increase, thereby increasing the vaporisation power threshold so as to tend to reduce vaporisation. This arrangement can be set up so that the motors 104 and 44 remain inactive until vaporisation is detected.

In an alternative mode, the pump motor 104 can be operated before vaporisation is detected, and indeed, before the generator 1 is switched on Thus, by detecting the presence of RF voltages at the output of the generator 1 using the RF active detection circuit 116, the pump can be activated by the microcontroller 112 for a preprogrammed duration in order to attract and remove loose tissue in the vicinity of the electrode 12 when the generator is switched on. However, by using the footswitch detection circuit 118 connected to the footswitch unit 5, and by controlling the actuation of the generator 1 by the microcontroller 112 via a line 126, a different operation sequence can be effected whereby, upon actuation of the footswitch unit, firstly the pump motor 104 is started before RF power is applied to the electrode 12, then a signal is fed to the generator via the line 126, after a predetermined interval, to actuate the output of the generator. This means that, instead of the pump controller being a slave unit to the RF generator 1 as first described above, the generator is a slave unit to the pump controller. Consequently, a boosted pump phase can be activated without RF power, so as to attract loose tissue before it is dispersed by the application of RF power.

FIGS. 5 and 6 show the second form of electrode unit E2. This instrument is a modification of that shown in FIGS. 2 and 3, and so like reference numerals will be used for like parts, and only the modifications will be described in detail. There are two main modifications, the first being to the drive to the rod 14, and the second to the configuration of the active electrode 12.

In the first modification, the motor 44 rotatably drives the rod 14 via a coupling assembly 42. As with the embodiment of FIGS. 2 and 3, the rod 14 passes through aligned apertures in the washer 34, the gland 36 and the delrin bush 38. The bush 38 is somewhat longer than the equivalent bush of the embodiment of FIGS. 2 and 3 extending to the end 32a of the sleeve 32. A slip ring 46a is provided to connect the connector 46 to the rod 14.

The other main modification is that the active electrode 12 (the free end of the tungsten rod 14—in this embodiment of 0.5 mm diameter) is bent back over the free end of the ceramic tube 18. The turned-back portion 12a of the electrode 12 constitutes a side effect electrode. An apertured region 20a is formed between the ceramic tip 20 and the active electrode 12, this region loading to the aspiration channel defined by the interior of the shaft 10.

Another modification is that the rod 14 is a flexible drive rod whose distal end portion is off-set with respect to the central longitudinal axis of the shaft 10. In use, when the generator 1 is turned on, the motor 44 begins to rotate, causing the rod 14 to rotate within the shaft 10. This rotation provides a mechanical agitation that is sufficient to dislodge any sublimation products which condense within the shaft. The off-set of the rod 14 results in an unstable oscillation being set up in the rod, which sweeps adherent tissue debris from the inner wall of the shaft 10.

Figure 7:
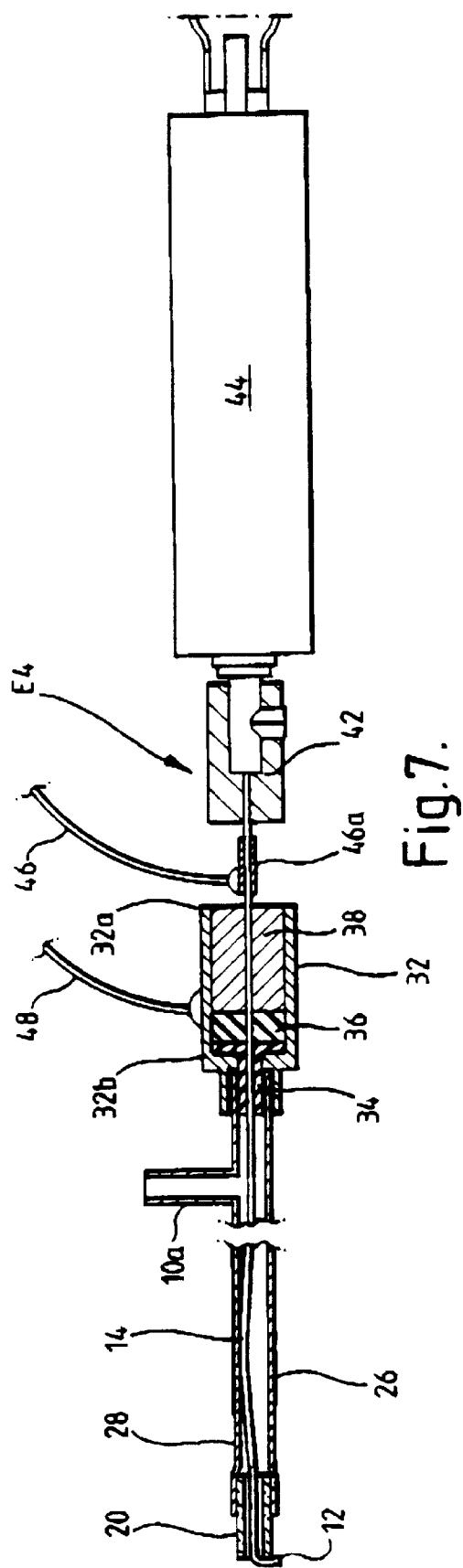
FIG. 7 is a diagrammatic side elevation, partially broken away, of a third form of electrode unit constructed in accordance with the invention.
Figure 8:
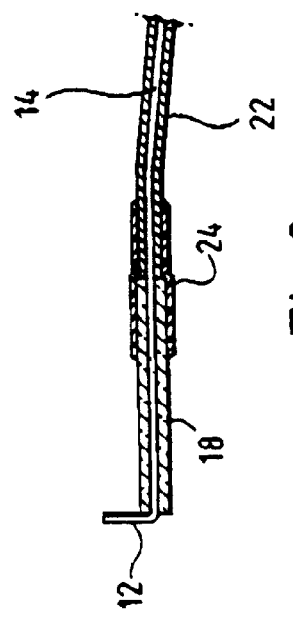
FIG. 8 is a diagrammatic side elevation of the electrode assembly of the electrode unit of FIG. 7.

FIGS. 7 and 8 show the third form of electrode unit E3. This unit E3 is a modification of the unit E2, so like reference numerals will be used for like parts, and only the modifications will be described in detail. The main modification is to the configuration of the active electrode assembly. Thus, as shown in FIG. 8, the active electrode 12 is shaped like a crank handle, and defines an elbow. 12b which is off-set from the axis of the ceramic tube 18. The ceramic tip 20 is formed with an inclined cam surface 20b which, in use, engages with the elbow 12b to force the tip of the active electrode 12 outwardly, and to ensure better tissue engagement. This crank handle configuration of the active electrode 12 also ensures that, as the tip rotates, the elbow 12b is pushed around the inner surface of the ceramic tip 20, thereby removing debris which would otherwise tend to build up there.

Figure 9:
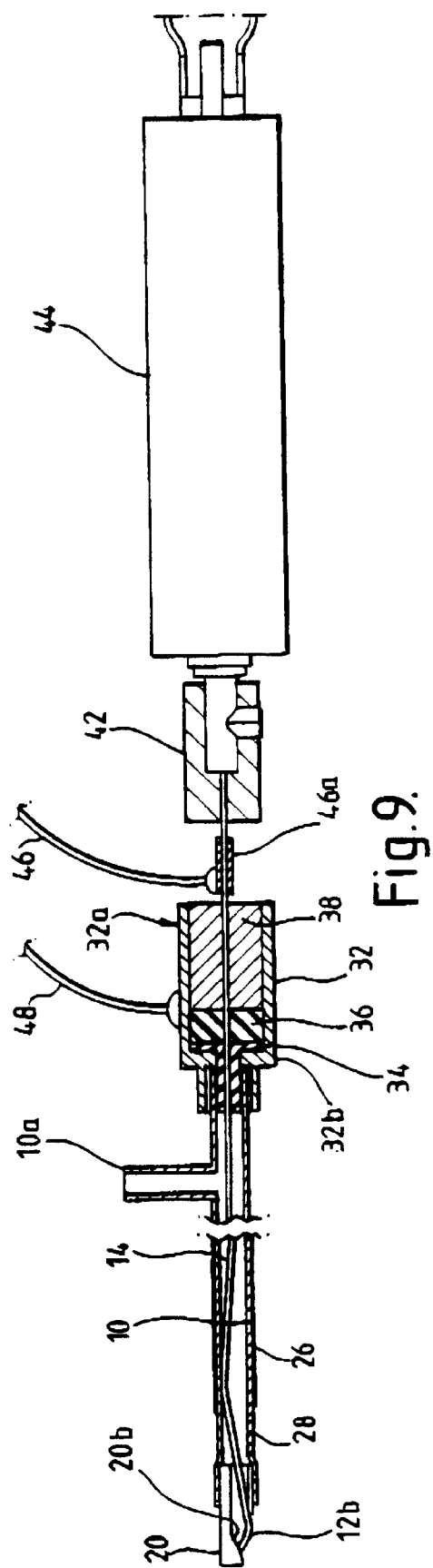
FIG. 9 is a diagrammatic side elevation, partially broken away, of a fourth form of electrode unit constructed in accordance with the invention.
Figure 10:
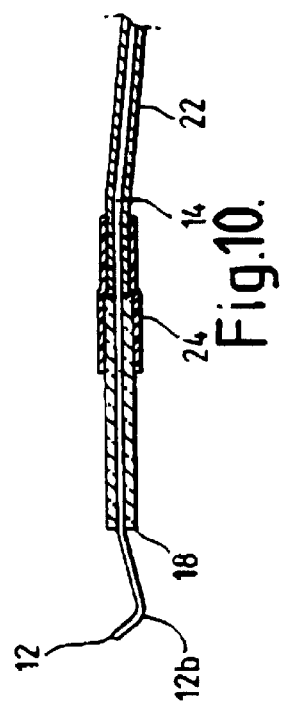
FIG. 10 is a diagrammatic side elevation of the electrode assembly of the electrode unit of FIG. 9.

FIGS. 9 and 10 show the fourth form of electrode unit E4. This unit E4 is also a modification of the unit E2, so like reference numerals will be used for like parts, and only the modifications will be described in detail. Here, the main modification is to the configuration of the active electrode 12 which, in this case, is an end effect electrode, being constituted by a simple hook-shaped end portion 12a at the end of the rod 14. As with the embodiments of FIGS. 5 and 6, the rod 14 is a flexible drive rod whose distal end portion off-set with respect to the central longitudinal axis of the shaft 10.

Figure 3:
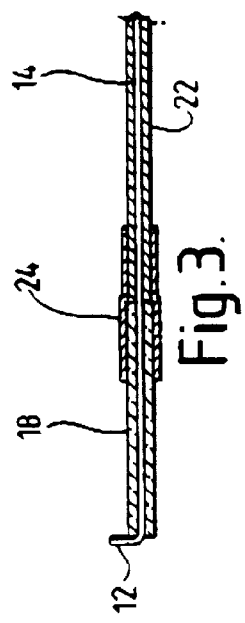
FIG. 3 is a diagrammatic side elevation of the electrode assembly of the electrode unit of FIG. 2.

As with the electrode unit E1 of FIGS. 2 and 3 the suction pump of each of the electrode units E2 to E4 can be pulsed to control the vaporisation power threshold at the active electrode 12 The control, circuit of FIG. 4 could be used for this purpose, the circuit in each of these cases being used to influence the vaporisation power threshold by rotating (instead of reciprocating) the active electrode 12 so as to produce turbulence in the surrounding saline solution, the rotation speed being controlled or being pulsed depending upon the degree to which the vaporisation threshold is to be altered.

As has already been described, the adherence of tissue over the active electrode 12 may induce a steady state condition, and the aspiration method must allow for removal of unvaporised tissue particles whilst not quenching vapour pocket formation. Rotation of the active electrode 12 of the electrode units E2 to E4 provides several advantages to overcome these performance issues. Thus, rotating the active electrode 12 increases the effective size of the electrode, as far as tissue contact area is concerned, for one complete rotation, whilst reducing the physical size of the active electrode. Reducing the size of the active electrode 12 reduces the vaporisation power threshold to a degree sufficient to enable aspiration along the axis of rotation when the generator control method is employed.

The introduction of rotation and aspiration through the active electrode 12, or more accurately through a channel within the range of motion of the active electrode, prevents the steady state being reached, and so prevents tissue bridging. This is achieved as tissue temporarily obstructing the aspiration channel is always treated, as opposed to positioning aspiration channels outside the range of motion of the active electrode 12, in which case only tissue adjacent to that obstructing the aspiration channel would be treated.

Given that the aspiration channel is required to cope with unvaporised tissue, the active electrode 12 is only required to incise the tissue such that the tip of the tissue in the aspiration channel is detached from the body of the tissue and then aspirated through the channel. Ideally, the truncated portion of tissue is also morcellated or partially vaporised by the active electrode 12 to reduce the size of tissue pieces. This morcellation is accomplished by introducing an off-set in the drive shaft/connector to the active electrode 12 which rotates in the aspiration channel of larger internal diameter than the external diameter of the connector, a feature which has additional advantages in preventing blocking of the aspiration channel, as is described below.

The relative contributions of tissue incision or morcellation and tissue vaporisation to the overall tissue debulking process can be controlled by the interaction of the bore of the terminal aspiration channel, the suction pressure and the bulk of the active electrode 12. Owing to the overall size constraints on the external diameter of the instrument it is, in general, the diameter of the drive rod 14 whose distal tip forms the active electrode 12 and which, therefore, also provides the means of electrical connection to the active electrode, which determines whether tissue removal occurs primarily by incision/morcellation or vaporisation. Typically a drive rod 14 (and hence active electrode 12) formed from 0.2–1.0 mm diameter tungsten wire provides incision/morcellation, and a drive rod active electrode formed from 0.5 mm diameter tungsten wire primarily provides vaporisation. The incision/morcellation technique has advantages when dealing with soft friable tissue, whereas the vaporisation technique has advantages when application is made to dense fibrous or cartilaginous tissue. The design can, therefore, be optimised for the type of tissue encountered during use in particular surgical specialities or, alternatively, a multi functional design with a drive rod and active electrode typically formed from 0.4–0.6 mm tungsten can be used.

For all four electrode units E1 to E4, agitation within the aspiration shaft 10 significantly reduces the risk of blockage, either by morcellated tissue, sublimated products of vaporisation or both. This can be accomplished by axial or rotary motion of the rod 14 which is positioned within the aspiration channel, with or without other means of fluid agitation, including the cycling of suction pressure, which may be provided as an integral feature of generator output, control of suction, and sonic pressure waves. To enhance the effect of agitation, it is beneficial to construct the drive rod 14 from a lubricious material to reduce adherence.

Each of the electrode units E1 and E4, has the additional advantage that the aspiration in the region of the active electrode 12 restricts the flow of convection currents in the saline surrounding the electrode assembly. As the power threshold required to reach vaporisation is dependent on the power dissipation of the active electrode 12 and the flow characteristics around it, the power threshold is dependent upon the maximum rate of convection. Consequently, the restriction of the convection currents reduces the power threshold and/or permits the use of higher saline flow rates, and this is advantageous as it enables the use of a cheaper RF generator, as well as avoiding problems such as dissipation within the instrument, and catastrophic overheating of the active electrode. It also facilitates control of the generator once vaporisation commences. The importance of power threshold of vaporisation is discussed in greater detail in the specification of our International Patent Application No. GB97/00065.

Moreover, each of the electrode units E1 to E4 is such as to prevent tissue bridging, as the tendency for tissue to obstruct the aspiration channel is, in each case, obviated by the movement of the active electrode ensuring that such tissue is treated. The movement of the active electrode 12 also ensures tissue morcellation, though this is effected by electrosurgery rather than by mechanical cutting.

It is a feature of each of the electrode units E1 to E4 that pieces of morcellated tissue separated from a surgical site will be drawn into the aspiration channel by the suction pressure. Should such pieces be too large to enter the aspiration channel, they will be reduced in size by a combination of the mechanical action of the agitated electrode 12 and the electrosurgical action created by the positioning of the return electrode 28 in relation to the aspiration channel. In the limit, the spacing of the return electrode 28 relative to the motion of the agitated electrode 12 can be adjusted to allow a controlled level of periodic arcing between the two. This aspect permits control of the relative strength of the mechanical and electrosurgical actions in keeping the aspiration channel clear. This aspect is described in greater detail in the specification of our British patent application 9814727.5.

It will be apparent that modifications could be made to the electrode units described above. For example, instead of providing an off-set drive rod 14, this rod could be loosely coiled so that the coils lie against the inner wall of the aspiration channel, whereby, during rotation, a worm screw action occurs to encourage proximal movement of tissue debris, as well as cleaning of the inner wall of the channel.

The motor 44 of each of the embodiments would be powered by the RF generator 1. This has the advantage that the motor 44 can be controlled by means that require the RF output voltage to exceed the vaporisation power threshold before sufficient power is delivered to energise the motor. Control means for the purpose could be mounted with the motor 44 within the handpiece 3.

It would also be possible to introduce axial motion during rotation. Thus, for the electrode unit E4, the simple 90 hook form active electrode 12 can rotate on a bearing surface provided by the distal end face of the ceramic tube 18, this end face being provided with ratchet teeth features. Thus, as the rod 14 rotates, the hook-shaped end portion 12a moves in and out as it engages and disengages the ratchet teeth, this axial movement being permitted by the off-set flexible drive rod 14 repeatedly elongating and shortening.

As an alternative to an electric motor, each of the units E1 to E4 could be powered by a fluid drive generated through a rotary vane or similar apparatus, which, in turn, may be powered by the suction means.

It is also possible to power the rotary drive by the RF generator 1, so that an integral and interactive system of the rotary drive, the active electrode 12, the RF generator and the suction means is provided.

The upper limit of the speed of rotation of the units E2 to E4 is defined at that level which elevates the vaporisation power threshold beyond the output range of the RF generator 1, which will, in turn, be dependent upon the geometry of the active electrode 12. Typically, the speed of tissue removal is increased with increased rotary speed when primarily employing the incision/morcellation technique, and is increased with decreased rotary speed when primarily employing the vaporisation technique. It is, therefore, evident that, in a multi-functional design, it is advantageous for the user to vary the rotary speed depending on the nature of the tissue being treated. To this end, a typical range of rotary speeds would be from 100 revs/min to 1000 revs/min.

With the rotary action electrode units E2 to E4, the effective size of the active electrode 12 is increased, and a significant aspect is the incision of tissue. The active electrode 12 is fabricated from the distal end of the drive rod 14, so simple wire form electrodes meet these performance requirements. The only drawback of these simple electrode forms is that asymmetry of the tissue contact can make it difficult to maintain an accurate location on a tissue surface, particularly when that surface is comprised of more fibrous or more dense tissue.

If the wire form active electrode 12 protrudes from the ceramic tube 18, for example in a simple loop form as with the electrode unit E2, then the potential exists for the loop to excise tissue pieces too large for aspiration through the distal opening of the aspiration channel. Should this occur, the exposed distal end of the drive rod 14 within the aspiration channel performs an important function in morcellating and vaporising such tissue pieces, so that they are reduced in size sufficiently to enter the aspiration channel. This function is enhanced by the eccentric motion of the drive rod 14 within the aspiration channel.

Whilst the amount of protrusion of the active electrode 12 from the distal end of the ceramic tube 18 is governed by the rules described in our International Patent Application GB96/01473, the effect of aspiration in increasing vaporisation threshold changes these rules. The other performance factor governing the dimension of the active electrode 12 is similar to that defining the diameter of the wire. Thus, the thinner wire forms, which are used on soft tissue, can protrude from the distal end of the ceramic tube 18 in the treatment axis; whilst the thicker wire forms, which are used on more dense tissue, ideally extend beyond the distal end of the ceramic tube in the treatment axis by an amount not exceeding the diameter of the wire. The active electrode 12 may also take on more convoluted or more complex generally planar forms of end effect electrodes and generally axial forms for side effect electrodes, for example coils, spirals, meshes or multiple spokes.

Our International Patent Application GB96/01472 describes a technique of introducing a conductive fluid to the region of a tissue treatment (active) electrode in order to define, in use, a conductive fluid path between the active electrode and a return electrode. The electrode units E1 to E4 of the present invention could be modified to incorporate those features. In particular, these units could be modified for use in gaseous operating environments, either on the surface of a body or within body cavities.

The specification of our British Patent Application 9612993.7 describes a technique of aspiration in the vicinity of a tissue treatment (active) electrode, wherein the suction pressure is controlled by generator output features in order to facilitate vaporisation by intermittently lowering the vaporisation threshold by cessation of suction flow. The techniques could advantageously be incorporated in the electrode units E1 to E4, both to ensure the vaporisation threshold is exceeded between suction pulses, and as a result of the suction pulsing assisting in preventing blockage of the aspiration channel.

As a suction pulse is initiated only once the vaporisation threshold has been exceeded, tissue can only be attracted to the active electrode once the threshold is exceeded by activation remote from the tissue within the surrounding distension medium. It is known that the vaporisation threshold is lowered once tissue is engaged by the active electrode. It is, therefore, advantageous for suction to be applied initially without RF activation as a variable time delay feature.

In summary the electrosurgical instrument of the invention has the following advantageous features:
1. A small active electrode surface which is able to treat large tissue areas by virtue of active electrode movement.
2. A small active electrode to enable vaporisation, despite the cooling effects created by aspiration.
3. A mechanical movement at the active electrode tip, compatible with material removal within the aspiration channel.
4. Aspiration operation is dependent upon the vaporisation condition.
5. At least the outside of the shaft 10 is coated with a non-stick material such as polytetrafluoroethylene—ideally the inside of the shaft as well.
6. Active electrode tip movement occurs across the face of the aspiration channel, so that any lodged tissue is electrosurgically morcellated.
7. Active electrode agitation is dependent upon the vaporisation condition.
8. Discontinuities within the agitator rod ensure that the internal surfaces of the shaft are cleaned; or the rod flexes sufficiently to create the same effect.
9. A ceramic-to-ceramic interface at the active electrode tip ensures that the internal circumference of the outer ceramic is wiped by the inner ceramic.
10. The agitator rod is independently insulated in ceramic at its tip.
11. Offset rotary action for a side-effect electrode to enable flat surface engagement.

Figure 11:
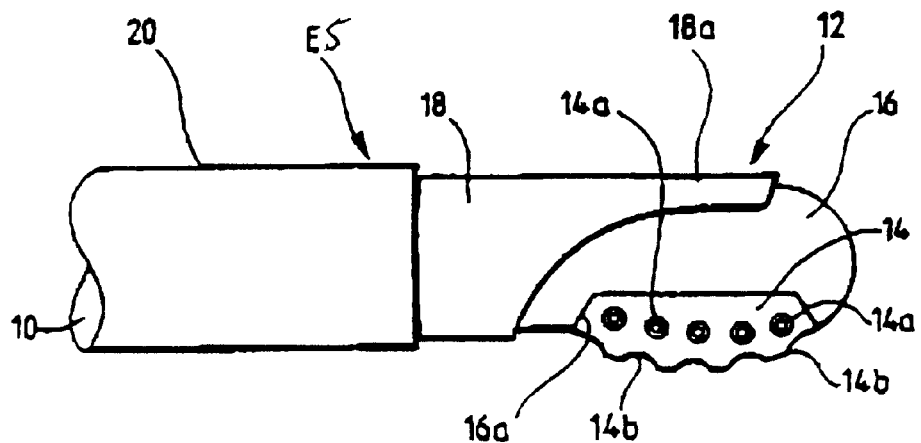
FIG. 11 is a diagrammatic side elevation of a fifth form of electrode unit constructed in accordance with the invention.

Embodiments of a further aspect of the present invention will now be described with reference to FIGS. 11 to 15. FIG. 11 shows a fifth form of electrode unit E5 for detachable fastening to the electrosurgical instrument handpiece 3, the electrode unit comprising a shaft 10, which is constituted by a semi-flexible tube made of stainless steel or phynox electroplated in copper or gold, with an electrode assembly 12 at a distal end thereof. At the other end (not shown) of the shaft 10, means are provided for connecting the electrode unit E5 to the handpiece 3 both mechanically and electrically.

As with the earlier embodiments, the RF generator 1 (not shown in FIG. 11) delivers an electrosurgical current to the electrode assembly 12. The generator 1 includes means for varying the delivered output power to suit different electrosurgical requirements. The generator may be as described in the specification of our European Patent Application 96304558.8 (the disclosure of which is hereby incorporated by reference).

The electrode unit E5 includes an active (tissue treatment) electrode 14 which is constituted by a curved fenestrated plate made of tungsten or an alloy of tungsten or platinum. The active electrode 14 is formed with a plurality of fenestrations 14a, and the regions 14b of the active electrode adjacent to the fenestrations define cup-shaped recesses (see FIG. 12). The active electrode 14 is connected to the RF generator 1 via an insulated central copper conductor (not shown). A ceramic insulation sleeve 16 surrounds the central conductor, the active electrode 14 extending laterally therefrom through a cut-out 16a. A return electrode 18, which is constituted by the distal end of the instrument shaft 10, surrounds the proximal end of the sleeve 16. An outer insulating coating 20 (which could be polyvinylidene fluoride, a polyimide, polytetrafluoroethylene, a polyefin, a polyester or ethylene tetrafluoroethylene) surrounds the proximal portion of the shaft adjacent to the return electrode 18. The return electrode 18 is formed with a hood-like extension 18a which extends over the surface of the sleeve 16 which is opposite to the cut-out 16a. The electrode unit E5 can, thus, provide maximum tissue engagement for shallow working angle applications, and is known as a side-effect electrode.

This electrosurgical instrument is particularly useful for rapid tissue debulking. One of the problems which could be encountered when tissue is rapidly debulked using an arthroscopic electrode configuration, particularly when working in small joint spaces, is the production of vapour bubbles generated as an end product of tissue vaporisation. Such bubbles obscure vision, and can coalesce at the site of tissue application, so that the electrical circuit between the active and return electrodes becomes compromised by the absence of conductive fluid. Irregular active electrodes having filamentary, mesh or coiled spring forms go some way to solving this problem as they reduce the vaporisation threshold as disclosed in the specification of our International Patent Application GB97/00065. Another advantage of these electrode forms is that the bubbles generated by vaporisation are smaller than those formed by solid electrodes. As the electrode 14 of this electrosurgical instrument is of irregular shape, it also has the advantage of producing relatively small vapour bubbles as the product of tissue vaporisation. The production of vapour bubbles is, however, further reduced as a result of the lower threshold power of vaporisation which results from use of the electrode unit E5. This improvement results from the hood-like extension 18a of the return electrode 18 which extends over the back of the active electrode 14a. This reduces the separation between the active electrode 14 and the return electrode 18, thereby reducing the electrical field and the vaporisation threshold power of the active electrode. This enhances the speed of vaporisation of the tissue at a lower power than would otherwise be required for the given active electrode area, and hence reduces the formation and liberation of vapour bubbles. As the hood-like extension 18a extends along the entire length of the active electrode 14, a large active electrode size can be supported, despite the reduction in electrode separation.

In order to reduce further the problems of vapour bubble production, the electrode unit E5 is provided with a suction pump (not shown) which can remove vapour bubbles via the shaft of the instrument through the fenestrations 14a in the active electrode 14. This enhances the elimination of vapour bubbles from an operation site, which is particularly advantageous during aggressive tissue debulking. The suction pump must be controlled so that the flow of bubbles through the electrode 14 is balanced to the voltage output characteristics of the RF generator 1 to prevent excessive cooling of the active electrode and a resultant increase in its vaporisation power threshold. The thermal mass of the fenestrated active electrode 14 is lower than that of a solid form active electrode, and this assists in rapidly re-establishing the vapour pocket around the active electrode should this collapse following excessive cooling. The cup-shaped recesses 14b in the active electrode 14 help to maintain the vapour pocket by retaining saline despite the fluid flow caused by the aspiration of the suction pump. The trapped saline absorbs energy, and so is vaporised in preference to the saline in the fluid flow caused by the aspiration.

The robustness of the electrode assembly 12 is also important in arthroscopic surgery, both because of the tendency of surgeons to use an electrode assembly as a cold manipulator, and because of the rigid nature of the tissue to be treated—particularly bone and cartilage. The hood-like extension 18a adds mechanical strength to the electrode assembly 12, as it extends over the ceramic insulation sleeve 16, thereby reducing the risk of ceramic fracture and potential breakdown of insulation. The electrode unit E5 is intended primarily for use in arthroscopic surgery which requires rapid tissue debulking by vaporisation. In use, the electrosurgical instrument is manipulated to introduce the electrode assembly 12 into a selected operation site (for example, within the joint space of a knee), so that the electrode 14 contacts the tissue to be treated, and with the tissue and the electrode assembly immersed in saline.

The footswitch 5b (or the push button 7b) is then operated to set the required power level for vaporisation. The generator 1 then provides sufficient RF power to the electrode assembly 12 to vaporise the saline surrounding the electrode 14, and to maintain a vapour pocket surrounding this electrode. Using a brushing technique, with firm pressure against the tissue surface, rapid debulking of the tissue is achieved. Gently touching the tissue will reduce the effect, and can be used to sculpture and smooth the residual tissue surface. With tissue engagement, provided the geometry of the active electrode 14 is appropriate for the application, the flow of irrigant through the active electrode will be reduced, the amount of reduction depending on the nature of the tissue surface, the application pressure and the suction pressure. Speed of debulking will, therefore, depend on these variables. Once the vaporisation occurs, the products will include vapour bubbles, carbon particles and tissue debris. All of these products are removed from the region of the action electrode 14 by aspiration caused by the suction pump. The fenestrations 14a are positioned so that vaporised tissue is drawn into the instrument, and then evacuated through the instrument shaft 10, by the aspiration of the suction pump.

The electrode unit E5 is also very effective in removing heated saline (distension fluid) from within a joint cavity. The risk of hot distension fluid occurs primarily during power application to reach the vaporisation threshold. Once the threshold has been reached, the power requirement falls by 30–50%.

Whilst aspiration through the active electrode 14 will remove heated saline from the body cavity, and remove any risk of overheating through prolonged activation under conditions where the vaporisation threshold is not reached, the cooling effect and disruption of vapour pockets created around the active electrode will increase the vaporisation threshold. A vicious cycle can, therefore, be created, wherein the more suction applied through the electrode 14, the more power required to reach the vaporisation threshold, and the greater the risk of heating. The other factor influencing the vaporisation threshold is the ratio of return active contact area, and the insulation separation between the two electrodes 14 and 18. The size of the active electrode 14 and the insulation separation must, therefore, be reduced to the minimum necessary to achieve the function in order to offset the effects of aspiration in elevating the power threshold of vaporisation.

The specification of our International Patent Application GB97/00065 discloses techniques for controlling the vaporisation threshold by employing active electrode designs which assist in capturing vapour pockets and preventing cooling of the active electrode application site by screening from the flow of irrigant provided by channels in an endoscope. The fenestrated electrode 14 of FIG. 11, which is reminiscent of a grater in which the holes are punched outwards from the inside, provides both the aspiration holes 14a and the areas 14b where the vapour pockets may be trapped, to reduce the vaporisation power threshold.

An alternative or supplementary method of reducing the vaporisation power threshold is to pulse the suction pressure, thereby allowing the threshold to be attained between pulses. Such pulses may be synchronised with the output features of the RF generator 1, both for safety reasons (if there is an occlusion of the suction channel), and to provide power bursts during active suction to sustain the vapour pocket, and clear any tissue occluding the fenestrations 14a in the active electrode 14.

A known technique in arthroscopic surgery is to apply suction through a mechanical, tissue-nibbling device, so that soft tissue present in the joint space, such as the infrapatellar fat pad, can be held in position within the nibbler jaws by suction whilst it is progressively "nibbled" away.

Attracting tissue to the active electrode 14 of the electrode unit E5 has a similar effect as, for the reasons already given above, compliant tissue adhering to the active electrode will result in a reduction of the vaporisation power threshold. Adherent tissue will be rapidly vaporised, and small tissue particles produced during vaporisation will be aspirated from the application site.

Because of its speed of debulking and side-effect configuration, the electrode unit E5 also has advantages in urological surgery as an EVAP technique for use in conjunction with a resectoscope. A resectoscope electrode unit is introduced very differently, in that it is mounted on an endoscope prior to passage of the assembled instrument through a working sheath introduced via the urethra. The proximal end of the electrode unit is connected to a trigger assembly and an electrical contact which is integral with the resectoscope. By this means, the electrode unit E5 can be moved back and forth through a defined range of motion by operating the trigger mechanism. As the electrode unit E5 is assembled prior to introduction, the size of the tip is not constrained by working channel dimensions, but rather by the diameter of the working sheath which can be up to 10 mm. Part of this diameter is occupied by the support wires to the electrode unit E5, which wires are commonly bent in a downward angle, with respect to the endoscopic image, to the working tip, so that they do not interfere with either visualisation or its operation. The electrode 14 can have a length lying within the range of from 3 mm to 4 mm and a width lying in the range of from 2 mm to 3 mm, and this size is necessary to urological surgery given that, on average, 20–30 grams of prostate tissue must be removed.

Because of the reservoir effect of the urinary bladder, and the mounting of the endoscope to view the tip of the active electrode 14 from below, bubble generation during vaporisation is less of a problem during endoscopic urology, as the bubbles flow away from the endoscope to accumulate in the bladder. Nevertheless, the use of the electrode unit E5 substantially reduces the possibility of bubble generation causing problems.

Although the electrode unit E5 is intended primarily for use in the vaporisation of tissue, it can also be used for desiccation, particularly of synovial membranes or to separate muscle attachments. In this case, once the electrode assembly 12 has been introduced into a selected operation site, the RF generator 1 is actuated using the footswitch 5a or the push button 7a to set the required power level for desiccation. The generator 1 will then provide sufficient RF power to the electrode assembly 12 to maintain the saline adjacent to the fenestrated electrode 14 substantially at its boiling point without creating a vapour pocket surrounding that electrode. The instrument can then be manipulated by moving the electrode 14 across the surface of the tissue to be treated in a side-to-side "painting" technique.

The electrode unit E5 can also be used for delivering a blended power output. This is achieved by automatically alternating the output of the RF generator 1 between the desiccation and vaporisation power levels, so that more haemostasis is produced then is possible in the vaporisation mode. As a consequence, the speed of tissue debulking is reduced, but the increased haemostasis is useful when cutting or debulking vascular tissue structures. Alternatively, the output of the RF generator 1 can be pulsed at the vaporisation power level, without cycled activation of the desiccation mode. This produces a less aggressive tissue vaporisation than occurs in the vaporisation mode, with a consequent reduction in both bubble formation and the risk of tissue charring.

Figure 13:
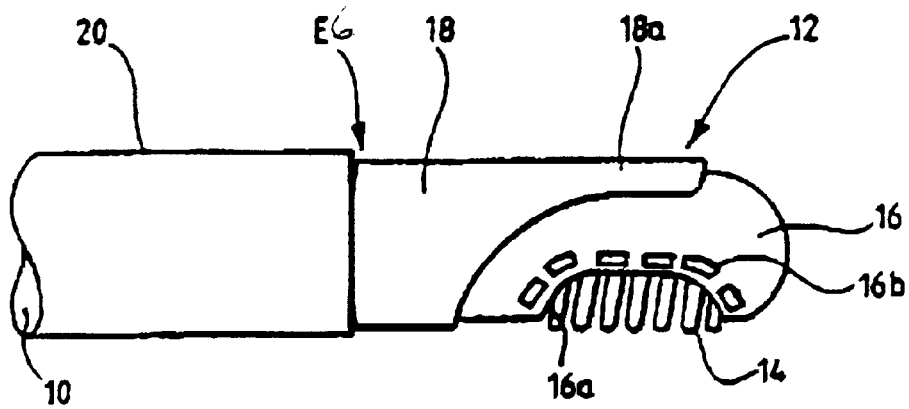
FIGS. 13 to 15 are diagrammatic side elevations of sixth, seventh and eighth forms of electrode unit constructed in accordance with the invention.
Figure 14:
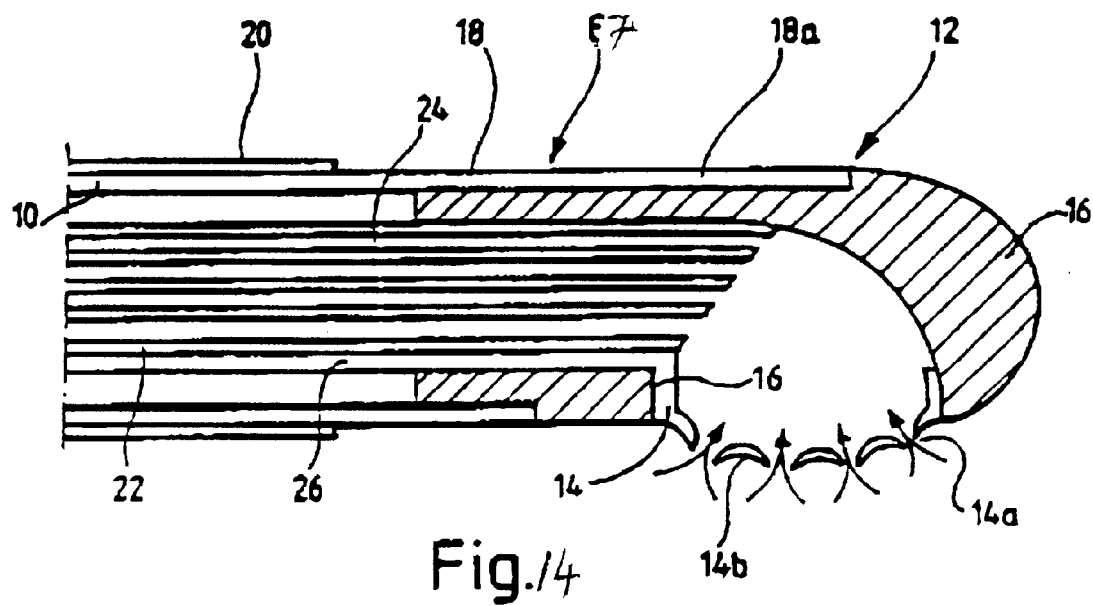
Figure 15:
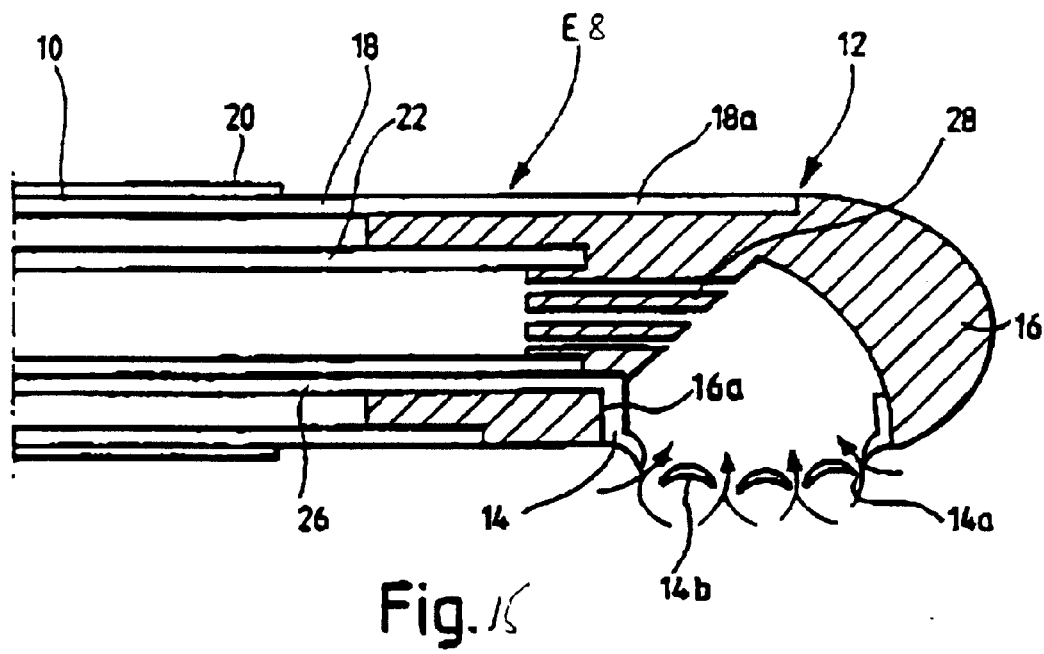

FIGS. 13 to 15 show electrode units E6 to E8 which are modified versions of the electrode unit E5. Accordingly, like reference numerals will be used for like parts, and only the modifications will be described in detail. Thus, the active electrode 14 of the electrode unit E6 is a coiled spring electrode mounted within the cut-out 16a. The coiled spring electrode 14 is made of tungsten or an alloy of tungsten or platinum, and its proximal end is connected to the RF generator 1 via an insulated central copper conductor (not shown). The electrode unit E6 is, however, provided with fenestrations 16b formed in the insulation sleeve 16, the fenestrations 16b being positioned all around, and adjacent to, the active electrode 14. These fenestrations 16b constitute the aspiration pathway for vapour bubbles, tissue and debris to be extracted, thereby enhancing the establishment of vapour pockets on the active electrode surface, and the inclusion of good vaporisation threshold properties, whilst ensuring good extraction of heated saline. The fenestrations 16b are positioned sufficiently close to the active electrode 14 to ensure that substantially all vaporised tissue is drawn into the instrument, and then evacuated through the instrument shaft 10, by the aspiration of the suction pump. In a modified version of this embodiment, the adjacent turns of the coiled spring electrode could define additional fenestrations for assisting with the aspiration of vapour bubbles, carbon particles and tissue debris.

Figure 12:
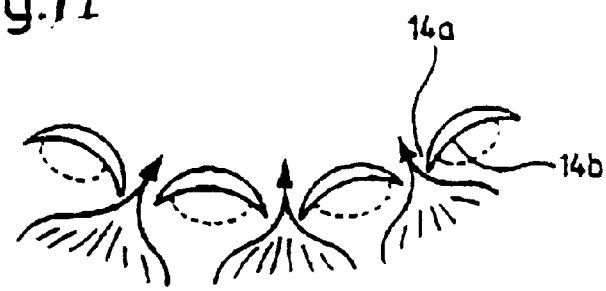
FIG. 12 is an enlarged view, looking in the direction of the arrow A of FIG. 11, of part of the fifth form of electrode unit.

The electrode unit E7 of FIG. 14 has a "grater" active electrode 14 similar to that of FIGS. 11 and 12. The instrument shaft 10 contains a multi-lumen tube 22 which defines a plurality of aspiration channels 24. The active electrode 14 is connected to the RF generator 1 by means of an insulated copper conductor 26. This embodiment has the advantage that, if a bolus of saline obstructs one or more of the channels 24, vapour can still be aspirated through the residual "open" channels 24. In this case, the bore of each channel 24 must not be narrower than the fenestrations 14a in the active electrode 14, thereby preventing obstruction of the channels by particulate debris generated at the tissue application site.

The electrode unit E8 of FIG. 15 includes a single-lumen tube 22 provided with an integral filter 28 at the distal end thereof. The filter 28 prevents obstruction of the lumen tube 22 by particulate debris generated at the tissue application site. Alternatively, the filter 28 could be formed integrally within the insulation sleeve 16 at the distal end of the tube 22. Again, the filter 28 could comprise a mesh having a small pore size for preferentially allowing de-gassing of the vaporisation products whilst accumulating solid material on the filter. In this case, gaseous extraction will be facilitated by the fact that the proximal single-lumen aspiration tube 22 can be constructed to withstand large vacuum pressures without collapsing. Here again, the active electrode 14 is connected to the RF generator 1 by means of an insulated copper conductor 26.

Each of the electrode units E5 to E8 has the additional advantage that the aspiration in the region of the active electrode 14 restricts the flow of convection currents in the saline surrounding the electrode assembly 12. As the power threshold required to reach vaporisation is dependent on the power dissipation of the active electrode 14 and the flow characteristics around it, the power threshold is dependent upon the maximum rate of convection. Consequently, the restriction of the convection currents reduces the power threshold, and this is advantageous as it enables the use of a cheaper RF generator, as well as avoiding problems such as dissipation within the instrument, and catastrophic overheating of the active electrode. It also facilitates control of the generator once vaporisation commences. The importance of power threshold of vaporisation is discussed in greater detail in the specification of our International Patent Application GB97/00065.

Another advantage of these electrode units is that, in use, the active electrode 14 faces down, so that saline heated thereby rises to the return electrode 18. This leads to a reduction of impedance throughout the circuit, and hence to a reduction of the heat dissipation in the saline path.

It will be apparent that modifications could be made to the embodiments described above. For example, the lumen tubes 22 of the embodiments of FIGS. 14 and 15 could be used with the electrode assembly 12 of FIG. 13, that is to say with the fenestrated insulation sleeve embodiment. It would also be possible to make the insulation sleeve 16 of each of the embodiments of a silicone rubber (such as a silicone polyurethane), glass, a polyimide or a thermoplastics material.

Throughout this specification, the term "pump" should be construed to include any suitable controlled vacuum source.

What is claimed is:

1. A method of operating an electrosurgical system comprising an electrosurgical generator which generates an oscillating radio frequency voltage across a pair of output terminals, and an electrosurgical instrument having a pair of electrodes supported relative to an instrument shaft, an aperture located in the region of at least one of the electrodes and a channel extending from the aperture for the aspiration of waste products from a treatment site, the electrodes being connected to the output terminals of the generator, the method comprising the steps of:

immersing the electrodes of the instrument in an electrically conductive fluid supplied to the treatment site;

applying, with the generator, a radio frequency oscillating voltage across the electrodes, causing an electrical current to flow through the conductive fluid, thereby boiling the fluid in the region of the electrodes and creating a vapour pocket;

manipulating the instrument shaft to cause tissue at the treatment site to encroach in the vapour pocket to thereby vapourise or cut said tissue;

applying suction from within the instrument shaft to aspirate waste products, along the shaft and away from the treatment site; and morcellating tissue which is bridging the aperture by agitating one of the electrodes relative to the aperture.

2. A method according to claim 1 wherein agitation of the electrode causes a corresponding agitation of the vapour pocket, and morcellation of the excised tissue occurs as a result of bridging tissue encroaching within the vapour pocket, and thereby being vapourised.

3. A method according to claim 2, further comprising the step of mechanically agitating sublimation products which condense within the channel, thereby to assist in the prevention of blockage thereof.

4. A method according to claim 1 wherein the electrode is agitated by rotation thereof about an axis substantially parallel with the shaft.

5. A method according to claim 1 wherein suction is applied in dependence upon the instantaneous output power of the generator, thereby to prevent quenching of the vapour pocket.

6. A method according to claim 1 wherein the electrodes are located on the instrument shaft.

7. A method according to claim 6 wherein the agitated electrode is located in the aperture, and is agitated by a cyclic motion thereof within the aperture.

8. A method of operating an electrosurgical system comprising an electrosurgical generator which generates an oscillating radio frequency voltage across a pair of output terminals, an electrosurgical instrument having a pair of electrodes supported relative to an instrument shaft, and a channel extending from an aperture located in the region of at least one of the electrodes, for the aspiration of waste products from a treatment site, the electrodes being connected to the output terminals of the generator, the method comprising the steps of:

immersing the electrodes of the instrument in an electrically conductive fluid supplied to the treatment site;

applying, with the generator, a radio frequency oscillating voltage across the electrodes, causing an electrical current to flow through the conductive fluid, and boiling the fluid in the region of the electrodes thereby creating a vapour pocket;

manipulating the instrument shaft to cause tissue at the treatment site to encroach in the vapour pocket to thereby vapourise or cut said tissue;

applying suction to aspirate waste products along the shaft and away from the treatment site; and morcellating tissue which is bridging the aperture by agitating one of the electrodes relative to the aperture thereby to agitate the vapour pocket, wherein morcellation of said bridging tissue occurs as a result of the agitation of the vapour pocket causing bridging tissue to encroach within the vapour pocket, and wherein agitation of the electrode is provided by a cyclical motion of the electrode within the aperture of the channel provided in the instrument shaft.

9. A method according to claim 8 wherein suction is applied in dependence upon the instantaneous output of the electrosurgical generator.

10. A method according to claim 8 wherein suction is only applied at times when radio frequency power is applied to the electrodes on the instrument.

11. A method according to claim 8 wherein agitation of said one of the electrodes occurs within the aperture.

12. A method according to claim 8 wherein the cyclical motion of said one of the electrodes is rotary motion thereof.

13. A method according to claim 8 further comprising the step of mechanically agitating sublimation products within the channel.

14. A method according to claim 8 wherein the electrically conducting fluid is isotonic saline.

15. A method of operating an electrosurgical system including an electrosurgical generator which generates an oscillating radio frequency output across a pair of output terminals, an electrosurgical instrument having a shaft and at least an active tissue treatment electrode located on the shaft and an aspiration channel which has an aperture in the region of the active electrode and by means of which waste products may be removed from the treatment site, the method comprising the steps of:

immersing the active electrode in an electrically conductive liquid supplied to the treatment site;

operating the generator to cause an alternating current to flow in the region of the active electrode; thereby heating the liquid, and creating a vapour pocket in the region of the active electrode;

manipulating the instrument to bring the vapour pocket into proximity with tissue in the region of the treatment site, thereby to vapourise tissue which encroaches within the vapour pocket;

applying suction to the channel to aspirate waste products away from the treatment site; and causing an agitation of the vapour pocket in order to move the vapour pocket relative to tissue bridging the aspiration channel, thereby to cause said bridging tissue to encroach the vapour pocket and to become vapourised.

16. A method according to claim 15 wherein the instrument further comprises a return electrode located on the shaft and insulated from the active electrode, and wherein alternating current flows between the active and return electrodes.

17. A method according to claim 15 wherein suction is applied to the aspiration channel in dependence upon an instantaneous output parameter of the generator.

18. A method according to claim 17, wherein the suction is controlled in order to prevent quenching of the vapour pocket.

19. A method according to claim 17 wherein suction is pulsed.

20. A method according to claim 15, wherein the active electrode is located in the aperture.

21. A method according to claim 20, wherein agitation of the vapour pocket is caused by agitation of the active electrode relative to the shaft.

22. A method according to claim 21, wherein agitation of the active electrode is provided by a cyclical motion thereof relative to the shaft.

23. A method according to claim 22, wherein the cyclical motion of the active electrode is a rotation of the active electrode relative to the shaft.

24. A method according to claim 15, wherein agitation of the vapour pocket is caused by varying the size of the vapour pocket.

* * * * *